(12) United States Patent
Parihar

(10) Patent No.: US 9,370,400 B2
(45) Date of Patent: Jun. 21, 2016

(54) CLIP APPLIER ADAPTED FOR USE WITH A SURGICAL ROBOT

(71) Applicant: ETHICON ENDO-SURGERY, INC., Cincinnati, OH (US)

(72) Inventor: Shaliendra Parihar, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 36 days.

(21) Appl. No.: 13/654,444

(22) Filed: Oct. 18, 2012

(65) Prior Publication Data
US 2013/0282021 A1    Oct. 24, 2013

Related U.S. Application Data

(60) Provisional application No. 61/548,989, filed on Oct. 19, 2011.

(51) Int. Cl.
*A61B 17/10* (2006.01)
*A61B 19/00* (2006.01)
*A61B 17/00* (2006.01)

(52) U.S. Cl.
CPC ....... *A61B 19/2203* (2013.01); *A61B 17/00234* (2013.01); *A61B 2019/2215* (2013.01)

(58) Field of Classification Search
CPC .................. A61B 19/2203; A61B 2019/2211; A61B 2019/2215; A61B 2019/2219; A61B 2019/2226; A61B 2019/2242; A61B 2019/2269; A61B 19/22; A61B 2017/00367; A61B 2017/00371; A61B 2017/00376; A61B 2017/00393; A61B 2017/00407; A61B 17/00234; A61B 2017/00327; A61B 2017/00323

USPC .................................................. 606/142, 143
See application file for complete search history.

(56) References Cited

U.S. PATENT DOCUMENTS

| 800,000 | A | 9/1905 | Melrose |
| 2,968,041 | A | 1/1961 | Skold |
| 3,459,029 | A | 8/1969 | Rosenfeld et al. |
| 4,038,987 | A | 8/1977 | Komiya |
| 4,064,881 | A | 12/1977 | Meredith |
| 4,080,820 | A | 3/1978 | Allen |
| 4,152,920 | A | 5/1979 | Green |
| 4,188,953 | A | 2/1980 | Klieman et al. |

(Continued)

FOREIGN PATENT DOCUMENTS

| AU | 2006201349 A1 | 11/2006 |
| AU | 2006213959 A1 | 3/2007 |

(Continued)

OTHER PUBLICATIONS

European Search Report for 06252082.0, dated Dec. 27, 2006 (6 pages).

(Continued)

*Primary Examiner* — Jonathan W Miles
*Assistant Examiner* — Chima Igboko

(57) ABSTRACT

A clip applier adapted for use with a surgical robot. The clip applier includes a shaft having clips stored therein and jaws adapted for receiving a clip from the shaft. The shaft is in mechanical communication with a robotic mounting portion that is adapted for mounting to a surgical robot. The robotic mounting portion contains a gear drive assembly for independently rotating the shaft, feeding clips into the jaws and forming clips in the jaws.

1 Claim, 28 Drawing Sheets

(56) References Cited

U.S. PATENT DOCUMENTS

| | | | |
|---|---|---|---|
| 4,242,902 | A | 1/1981 | Green |
| 4,296,751 | A | 10/1981 | Blake, III et al. |
| 4,298,072 | A | 11/1981 | Baker et al. |
| 4,349,028 | A | 9/1982 | Green |
| 4,372,316 | A | 2/1983 | Blake, III et al. |
| 4,408,603 | A | 10/1983 | Blake, III et al. |
| 4,448,193 | A | 5/1984 | Ivanov |
| 4,449,530 | A | 5/1984 | Bendel et al. |
| 4,452,376 | A | 6/1984 | Klieman et al. |
| 4,513,746 | A * | 4/1985 | Aranyi et al. ............... 606/220 |
| 4,522,207 | A | 6/1985 | Klieman et al. |
| 4,532,925 | A | 8/1985 | Blake, III |
| 4,556,058 | A | 12/1985 | Green |
| 4,557,263 | A | 12/1985 | Green |
| 4,576,165 | A | 3/1986 | Green et al. |
| 4,588,580 | A | 5/1986 | Gale et al. |
| 4,590,937 | A | 5/1986 | Deniega |
| 4,611,595 | A | 9/1986 | Klieman et al. |
| 4,616,650 | A | 10/1986 | Green et al. |
| 4,651,737 | A | 3/1987 | Deniega |
| 4,662,374 | A | 5/1987 | Blake, III |
| 4,674,504 | A | 6/1987 | Klieman et al. |
| 4,676,504 | A | 6/1987 | Ponza |
| 4,702,274 | A | 10/1987 | Kramer |
| 4,712,549 | A | 12/1987 | Peters et al. |
| 4,741,336 | A | 5/1988 | Failla et al. |
| 4,799,481 | A | 1/1989 | Transue et al. |
| 4,834,096 | A | 5/1989 | Oh et al. |
| 4,844,066 | A | 7/1989 | Stein |
| 4,850,355 | A * | 7/1989 | Brooks et al. ............... 606/143 |
| 4,976,722 | A | 12/1990 | Failla |
| 4,979,950 | A | 12/1990 | Transue et al. |
| 5,009,661 | A | 4/1991 | Michelson |
| 5,012,666 | A | 5/1991 | Chen et al. |
| 5,030,226 | A | 7/1991 | Green et al. |
| 5,047,038 | A | 9/1991 | Peters et al. |
| 5,049,152 | A | 9/1991 | Simon et al. |
| 5,062,846 | A | 11/1991 | Oh et al. |
| 5,084,057 | A | 1/1992 | Green et al. |
| 5,086,901 | A | 2/1992 | Petronis et al. |
| 5,100,416 | A | 3/1992 | Oh et al. |
| 5,100,420 | A | 3/1992 | Green et al. |
| 5,104,395 | A | 4/1992 | Thornton et al. |
| 5,112,343 | A | 5/1992 | Thornton |
| 5,116,349 | A | 5/1992 | Aranyi |
| 5,127,730 | A | 7/1992 | Brelje et al. |
| 5,129,885 | A | 7/1992 | Green et al. |
| 5,156,609 | A | 10/1992 | Nakao et al. |
| 5,163,945 | A | 11/1992 | Ortiz et al. |
| 5,171,247 | A | 12/1992 | Hughett et al. |
| 5,171,249 | A | 12/1992 | Stefanchik et al. |
| 5,190,203 | A | 3/1993 | Rodak |
| 5,192,288 | A | 3/1993 | Thompson et al. |
| 5,197,970 | A | 3/1993 | Green et al. |
| 5,201,746 | A | 4/1993 | Shichman |
| 5,222,961 | A | 6/1993 | Nakao et al. |
| 5,232,450 | A | 8/1993 | Green et al. |
| 5,246,450 | A | 9/1993 | Thornton et al. |
| 5,269,790 | A | 12/1993 | Funatsu |
| 5,269,792 | A | 12/1993 | Kovac et al. |
| 5,270,171 | A | 12/1993 | Cercek et al. |
| 5,282,807 | A | 2/1994 | Knoepfler |
| 5,282,808 | A | 2/1994 | Kovac et al. |
| 5,286,255 | A | 2/1994 | Weber |
| 5,300,081 | A | 4/1994 | Young et al. |
| 5,306,149 | A | 4/1994 | Schmid et al. |
| 5,336,232 | A | 8/1994 | Green et al. |
| 5,354,304 | A | 10/1994 | Aleen et al. |
| 5,358,506 | A | 10/1994 | Green et al. |
| 5,366,458 | A | 11/1994 | Korthoff et al. |
| 5,382,254 | A | 1/1995 | McGarry et al. |
| 5,382,255 | A | 1/1995 | Castro et al. |
| 5,383,880 | A | 1/1995 | Hooven |
| 5,383,881 | A | 1/1995 | Green et al. |
| 5,395,381 | A | 3/1995 | Green et al. |
| 5,403,326 | A | 4/1995 | Harrison et al. |
| 5,403,327 | A | 4/1995 | Thornton et al. |
| 5,409,498 | A | 4/1995 | Braddock et al. |
| 5,423,835 | A | 6/1995 | Green et al. |
| 5,431,667 | A | 7/1995 | Thompson et al. |
| 5,431,668 | A | 7/1995 | Burbank, III et al. |
| 5,431,669 | A | 7/1995 | Thompson et al. |
| 5,433,721 | A | 7/1995 | Hooven et al. |
| 5,434,081 | A | 7/1995 | Maekawa |
| 5,439,156 | A | 8/1995 | Grant et al. |
| 5,468,250 | A | 11/1995 | Paraschac et al. |
| 5,470,007 | A | 11/1995 | Plyley et al. |
| 5,474,732 | A | 12/1995 | Korthoff et al. |
| 5,484,095 | A | 1/1996 | Green et al. |
| 5,484,451 | A | 1/1996 | Akopov et al. |
| 5,496,333 | A | 3/1996 | Sackier et al. |
| 5,497,933 | A | 3/1996 | DeFonzo et al. |
| 5,499,998 | A | 3/1996 | Meade |
| 5,501,693 | A | 3/1996 | Gravener |
| 5,509,920 | A | 4/1996 | Phillips et al. |
| 5,514,149 | A | 5/1996 | Green et al. |
| 5,527,318 | A | 6/1996 | McGarry |
| 5,527,319 | A | 6/1996 | Green et al. |
| 5,527,320 | A | 6/1996 | Carruthers et al. |
| 5,542,949 | A | 8/1996 | Yoon |
| 5,547,117 | A | 8/1996 | Hamblin et al. |
| 5,547,474 | A | 8/1996 | Kloeckl et al. |
| 5,562,694 | A | 10/1996 | Sauer et al. |
| 5,575,206 | A | 11/1996 | Szyszko |
| 5,575,806 | A | 11/1996 | Nakao et al. |
| 5,580,067 | A | 12/1996 | Hamblin et al. |
| 5,582,615 | A | 12/1996 | Foshee et al. |
| 5,582,617 | A | 12/1996 | Klieman et al. |
| 5,591,178 | A | 1/1997 | Green et al. |
| 5,594,798 | A | 1/1997 | Cox et al. |
| 5,601,224 | A | 2/1997 | Bishop et al. |
| 5,601,573 | A | 2/1997 | Fogelberg et al. |
| 5,605,272 | A | 2/1997 | Witt et al. |
| 5,607,273 | A | 3/1997 | Kecmer et al. |
| 5,607,436 | A | 3/1997 | Pratt et al. |
| 5,618,291 | A | 4/1997 | Thompson et al. |
| 5,624,452 | A | 4/1997 | Yates |
| 5,625,592 | A | 4/1997 | Shinozaki |
| 5,626,585 | A | 5/1997 | Mittelstadt et al. |
| 5,626,586 | A | 5/1997 | Pistl et al. |
| 5,630,539 | A | 5/1997 | Plyley et al. |
| RE35,525 | E | 6/1997 | Stefanchik et al. |
| 5,634,930 | A | 6/1997 | Thornton et al. |
| 5,643,291 | A | 7/1997 | Pier et al. |
| 5,645,551 | A | 7/1997 | Green et al. |
| 5,667,517 | A | 9/1997 | Hooven |
| 5,673,841 | A | 10/1997 | Schulze et al. |
| 5,681,330 | A | 10/1997 | Hughett et al. |
| 5,695,502 | A | 12/1997 | Pier et al. |
| 5,697,543 | A | 12/1997 | Burdorff |
| 5,700,270 | A | 12/1997 | Peyser et al. |
| 5,700,271 | A | 12/1997 | Whitfield et al. |
| 5,706,824 | A | 1/1998 | Whittier |
| 5,713,911 | A | 2/1998 | Racenet et al. |
| 5,720,756 | A | 2/1998 | Green et al. |
| 5,725,537 | A | 3/1998 | Green et al. |
| 5,725,538 | A | 3/1998 | Green et al. |
| 5,749,881 | A | 5/1998 | Sackier et al. |
| 5,755,726 | A | 5/1998 | Pratt et al. |
| 5,772,673 | A | 6/1998 | Cuny et al. |
| 5,776,147 | A | 7/1998 | Dolendo |
| 5,792,149 | A | 8/1998 | Sherts et al. |
| 5,792,150 | A | 8/1998 | Pratt et al. |
| 5,792,165 | A | 8/1998 | Klieman et al. |
| 5,794,834 | A | 8/1998 | Hamblin et al. |
| 5,830,221 | A | 11/1998 | Stein et al. |
| 5,833,695 | A | 11/1998 | Yoon |
| 5,833,696 | A | 11/1998 | Whitfield et al. |
| 5,833,881 | A | 11/1998 | Roe |
| 5,843,097 | A | 12/1998 | Mayenberger et al. |
| 5,843,101 | A | 12/1998 | Fry |
| 5,849,019 | A | 12/1998 | Yoon |
| 5,855,311 | A | 1/1999 | Hamblin et al. |
| 5,868,759 | A | 2/1999 | Peyser et al. |

(56) References Cited

U.S. PATENT DOCUMENTS

| | | |
|---|---|---|
| 5,868,761 A | 2/1999 | Nicholas et al. |
| 5,869,435 A | 2/1999 | Kelly et al. |
| 5,895,394 A | 4/1999 | Kienzle et al. |
| 5,902,312 A | 5/1999 | Frater et al. |
| 5,904,693 A | 5/1999 | Dicesare et al. |
| 5,928,251 A | 7/1999 | Aranyi et al. |
| 5,938,667 A | 8/1999 | Peyser et al. |
| 5,941,439 A | 8/1999 | Kammerer |
| 5,972,003 A | 10/1999 | Rousseau et al. |
| 5,993,465 A | 11/1999 | Shipp et al. |
| RE36,720 E | 5/2000 | Green et al. |
| 6,059,799 A | 5/2000 | Aranyi et al. |
| 6,063,097 A | 5/2000 | Oi et al. |
| 6,066,145 A | 5/2000 | Wurster |
| 6,096,058 A | 8/2000 | Boche et al. |
| 6,139,555 A | 10/2000 | Hart et al. |
| 6,152,920 A | 11/2000 | Thompson et al. |
| 6,217,590 B1 | 4/2001 | Levinson |
| 6,228,097 B1 | 5/2001 | Levinson et al. |
| 6,241,740 B1 | 6/2001 | Davis et al. |
| 6,277,131 B1 | 8/2001 | Kalikow |
| 6,306,149 B1 | 10/2001 | Meade |
| 6,306,150 B1 | 10/2001 | Levinson |
| 6,423,079 B1 | 7/2002 | Blake, III |
| 6,440,144 B1 | 8/2002 | Bacher |
| 6,458,142 B1 | 10/2002 | Faller et al. |
| 6,460,749 B1 | 10/2002 | Levinson et al. |
| 6,462,345 B1 | 10/2002 | Simon et al. |
| 6,507,400 B1 | 1/2003 | Pina et al. |
| 6,533,157 B1 | 3/2003 | Whitman |
| 6,537,289 B1 | 3/2003 | Kayan et al. |
| 6,544,271 B1 | 4/2003 | Adams et al. |
| 6,548,142 B1 | 4/2003 | Kar et al. |
| 6,548,796 B1 | 4/2003 | Silvermintz et al. |
| 6,549,275 B1 | 4/2003 | Cabuz et al. |
| 6,569,171 B2 | 5/2003 | DeGuillebon et al. |
| 6,589,792 B1 | 7/2003 | Malachowski |
| 6,597,438 B1 | 7/2003 | Cabuz et al. |
| 6,610,073 B1 | 8/2003 | Levinson |
| 6,646,742 B1 | 11/2003 | Gangstead et al. |
| 6,673,083 B1 | 1/2004 | Kayan et al. |
| 6,687,052 B1 | 2/2004 | Wilson et al. |
| 6,695,854 B1 | 2/2004 | Kayan et al. |
| 6,727,071 B1 | 4/2004 | Dunlay et al. |
| 6,752,823 B2 | 6/2004 | Prestel et al. |
| 6,869,435 B2 | 3/2005 | Blake, III |
| 6,911,033 B2 | 6/2005 | de Guillebon et al. |
| 7,052,504 B2 | 5/2006 | Hughett |
| 7,211,092 B2 | 5/2007 | Hughett |
| 7,261,724 B2 | 8/2007 | Molitor et al. |
| 7,288,098 B2 | 10/2007 | Huitema et al. |
| 7,297,149 B2 | 11/2007 | Vitali et al. |
| 7,637,917 B2 * | 12/2009 | Whitfield et al. ............ 606/143 |
| 7,686,820 B2 | 3/2010 | Huitema et al. |
| 7,691,098 B2 * | 4/2010 | Wallace et al. .................. 606/1 |
| 7,731,641 B1 | 6/2010 | Chen |
| 7,731,724 B2 | 6/2010 | Huitema et al. |
| 7,740,641 B2 | 6/2010 | Huitema |
| 7,875,029 B1 * | 1/2011 | Hausen ........................... 606/52 |
| 8,038,686 B2 | 10/2011 | Huitema et al. |
| 8,075,571 B2 | 12/2011 | Vitali et al. |
| 8,128,643 B2 * | 3/2012 | Aranyi et al. ................. 606/143 |
| 8,216,257 B2 | 7/2012 | Huitema et al. |
| 8,236,012 B2 | 8/2012 | Molitor et al. |
| 8,262,679 B2 | 9/2012 | Nguyen |
| 8,267,945 B2 | 9/2012 | Nguyen et al. |
| 8,640,788 B2 | 2/2014 | Dachs, II et al. |
| 2002/0099388 A1 | 7/2002 | Mayenberger |
| 2002/0123767 A1 | 9/2002 | Prestel |
| 2002/0128668 A1 | 9/2002 | Manetakis et al. |
| 2002/0138086 A1 | 9/2002 | Sixto et al. |
| 2002/0177863 A1 | 11/2002 | Mandel et al. |
| 2002/0198539 A1 * | 12/2002 | Sixto et al. ................... 606/142 |
| 2002/0198541 A1 | 12/2002 | Smith et al. |
| 2003/0014060 A1 | 1/2003 | Wilson et al. |
| 2003/0023249 A1 | 1/2003 | Manetakis |
| 2003/0040756 A1 | 2/2003 | Field |
| 2003/0040759 A1 | 2/2003 | deGuillebon et al. |
| 2003/0065358 A1 | 4/2003 | Frecker et al. |
| 2003/0069474 A1 | 4/2003 | Couvillon |
| 2003/0135224 A1 | 7/2003 | Blake |
| 2003/0191478 A1 | 10/2003 | Kortenbach et al. |
| 2004/0087979 A1 | 5/2004 | Field et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0153107 A1 | 8/2004 | Kayan et al. |
| 2004/0167545 A1 | 8/2004 | Sadler et al. |
| 2005/0049616 A1 | 3/2005 | Rivera et al. |
| 2006/0235436 A1 | 10/2006 | Anderson et al. |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235443 A1 | 10/2006 | Huitema et al. |
| 2006/0235444 A1 | 10/2006 | Huitema et al. |
| 2007/0089557 A1 | 4/2007 | Solomon et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0065116 A1 * | 3/2008 | Lee et al. ...................... 606/142 |
| 2008/0281336 A1 * | 11/2008 | Zergiebel .................... 606/142 |
| 2010/0185215 A1 | 7/2010 | Huitema et al. |
| 2010/0204717 A1 * | 8/2010 | Knodel ......................... 606/143 |
| 2010/0249804 A1 | 9/2010 | Huitema |
| 2011/0071543 A1 * | 3/2011 | Prisco et al. .................. 606/130 |
| 2011/0087241 A1 | 4/2011 | Nguyen |
| 2011/0087243 A1 | 4/2011 | Nguyen et al. |
| 2011/0218553 A1 | 9/2011 | Huitema et al. |
| 2011/0218555 A1 | 9/2011 | Huitema |
| 2011/0218556 A1 | 9/2011 | Nguyen et al. |
| 2011/0224696 A1 | 9/2011 | Huitema et al. |

FOREIGN PATENT DOCUMENTS

| | | |
|---|---|---|
| CN | 1994233 A | 7/2007 |
| CN | 100506177 C | 7/2009 |
| CN | 100522080 C | 8/2009 |
| CN | 100589774 C | 2/2010 |
| DE | 3490145 T1 | 5/1985 |
| DE | 4015562 A1 | 11/1991 |
| DE | 4303544 A1 | 9/1993 |
| DE | 19534320 C1 | 2/1997 |
| DE | 19537299 A1 | 4/1997 |
| DE | 19643073 A1 | 4/1997 |
| DE | 19647354 A1 | 5/1998 |
| DE | 19731453 A1 | 2/1999 |
| DE | 19933672 A1 | 2/2001 |
| EP | 0090815 A1 | 10/1983 |
| EP | 0152226 A1 | 8/1985 |
| EP | 0286921 A1 | 10/1988 |
| EP | 0409569 B1 | 1/1991 |
| EP | 0500353 A1 | 8/1992 |
| EP | 0510826 B1 | 10/1992 |
| EP | 0671148 A2 | 9/1995 |
| EP | 0674876 A2 | 10/1995 |
| EP | 0681810 B1 | 11/1995 |
| EP | 0704190 B1 | 4/1996 |
| EP | 0769274 B1 | 4/1997 |
| EP | 0832605 B1 | 4/1998 |
| EP | 0834286 B1 | 4/1998 |
| EP | 0908152 B1 | 4/1999 |
| EP | 1317906 B1 | 6/2003 |
| EP | 1405601 A1 | 4/2004 |
| EP | 1522264 A1 | 4/2005 |
| EP | 1537883 B1 | 6/2005 |
| EP | 1712188 B1 | 10/2006 |
| EP | 1712190 A2 | 10/2006 |
| EP | 1764043 B1 | 3/2007 |
| EP | 1764044 B1 | 3/2007 |
| EP | 1764045 B1 | 3/2007 |
| EP | 1913881 A1 | 4/2008 |

(56) References Cited

FOREIGN PATENT DOCUMENTS

| | | |
|---|---|---|
| EP | 2289431 B1 | 7/2012 |
| HK | 1100159 A1 | 11/2009 |
| HK | 1104438 A1 | 11/2009 |
| JP | 59067943 A | 4/1984 |
| JP | 62002528 A | 1/1987 |
| JP | H05505732 A | 8/1993 |
| JP | 7047070 A | 2/1995 |
| JP | 7299075 A | 11/1995 |
| JP | 9224947 A | 9/1997 |
| JP | 11192239 A | 7/1999 |
| JP | 2002535030 A | 10/2002 |
| JP | 2004500190 A | 1/2004 |
| JP | 2004305591 A | 11/2004 |
| JP | 2004534591 A | 11/2004 |
| JP | 2004535236 A | 11/2004 |
| MX | 06010632 A | 3/2007 |
| MX | 06010634 A | 3/2007 |
| MX | 06010633 A | 6/2007 |
| WO | WO 89/10094 A1 | 11/1989 |
| WO | WO 9608203 A1 | 3/1996 |
| WO | WO 99/02090 A1 | 1/1999 |
| WO | WO 00/42922 A1 | 7/2000 |
| WO | WO 01/26705 A2 | 4/2001 |
| WO | WO 01/56455 A2 | 8/2001 |
| WO | WO 02/15797 A1 | 2/2002 |
| WO | WO 02/28268 A2 | 4/2002 |
| WO | WO 03/005878 A2 | 1/2003 |
| WO | WO 03/005911 A1 | 1/2003 |
| WO | WO 2004/050971 A2 | 6/2004 |

OTHER PUBLICATIONS

European Search Report for 06252078.8, dated Dec. 27, 2006 (6 pages).
European Search Report for 0625479.3, dated Feb. 16, 2009 (8 pages).
European Search Report for 06254793.0, dated Oct. 1, 2009 (6 pages).
European Search Report for 06254800.3, dated Jan. 15, 2007 (6 pages).
European Search Report for 10179717.3, dated Nov. 19, 2010 (5 pages).
European Search Report for 10179741.3, dated May 25, 2011.
European Search Report for 10179743.9, dated Feb. 7, 2011 (10 pages).
Partial European Search Report for 10179741.3, dated Nov. 5, 2010 (6 pages).
International Preliminary Report dated Apr. 22, 2014; International Application No. PCT/US2012/060784.

* cited by examiner

CLIP APPLIER ADAPTED FOR USE WITH A SURGICAL ROBOT

CROSS REFERENCE TO RELATED APPLICATION

The present application claims the benefit of Provisional Application Ser. No. 61/548,989, filed Oct. 19, 2011.

BACKGROUND

The present disclosure relates generally to the field of robotic surgery. In particular, the present disclosure relates to, although not exclusively, robotically controlled surgical instruments. More particularly, the present disclosure relates to, although not exclusively, robotically controlled clip applier instruments having robotically controlled features for robotically feeding and forming surgical clips the surgical instrument.

Many surgical procedures require ligating blood vessels or other internal tissue. Many surgical procedures are performed using minimally invasive techniques where a hand-held instrument is used by the surgeon to perform the cutting or ligating.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
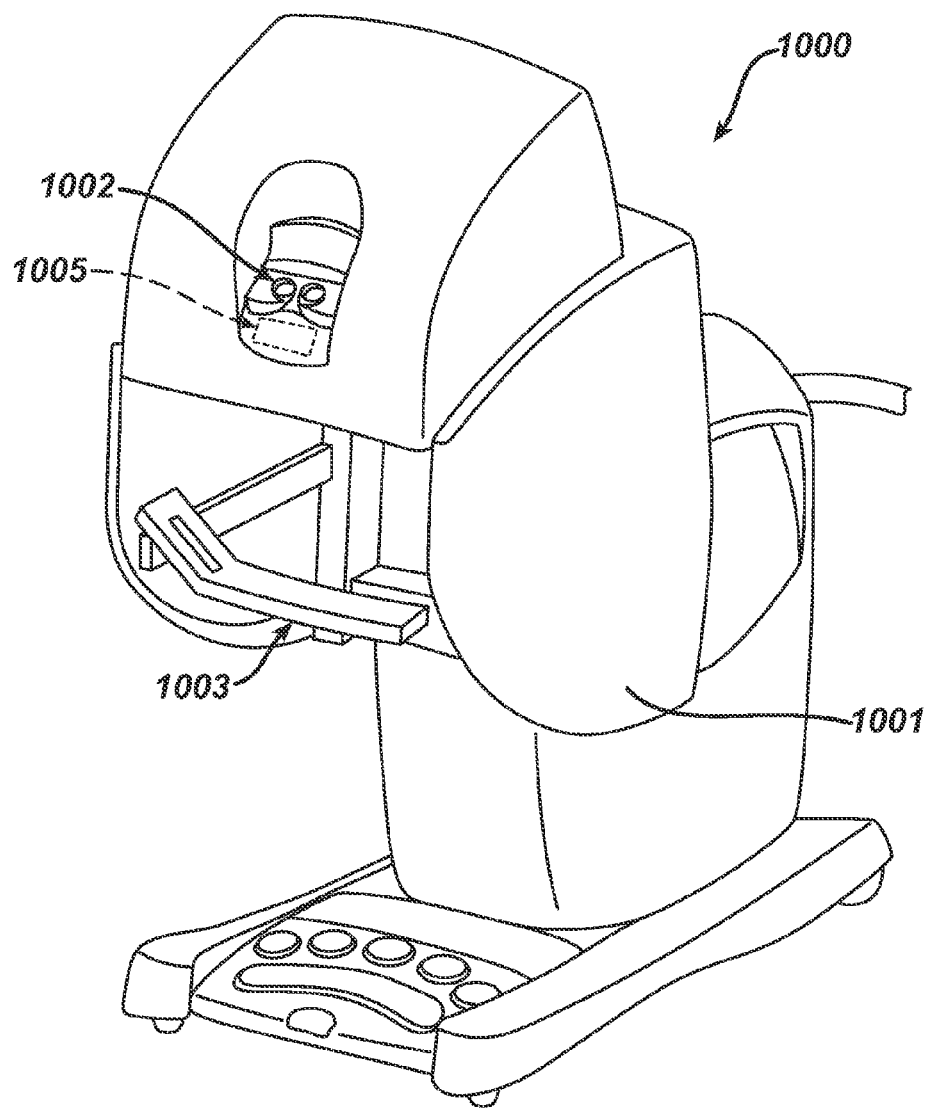
FIG. 1 is an isometric view of a robotic master control station.

Uses of the phrases "in various embodiments," "in some embodiments," "in one embodiment", or "in an embodiment", or "in an expression" or the like, throughout the specification are not necessarily all referring to the same embodiment. Furthermore, the particular features, structures, or characteristics of one or more embodiments may be combined in any suitable manner in one or more other embodiments. Such modifications and variations are intended to be included within the scope of the present invention.

The present invention generally provides a surgical clip applier and methods for using a surgical clip applier to apply surgical clips to a vessel, duct, shunt, etc., during a surgical procedure. An exemplary surgical clip applier can include a variety of features to facilitate application of a surgical clip, as described herein and illustrated in the drawings. However, a person skilled in the art will appreciate that the surgical clip applier can include only some of these features and/or it can include a variety of other features known in the art. The surgical clip applier described herein is merely intended to represent certain exemplary embodiments.

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524, 320, entitled "Mechanical Actuator Interface System For Robotic Surgical Tools", U.S. Pat. No. 7,691,098, entitled "Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Wristed Monopolar Electrosurgical End Effectors". Many of such systems, however, have in the past been unable to mechanically ligate vessels and tissue.

Figure 2:
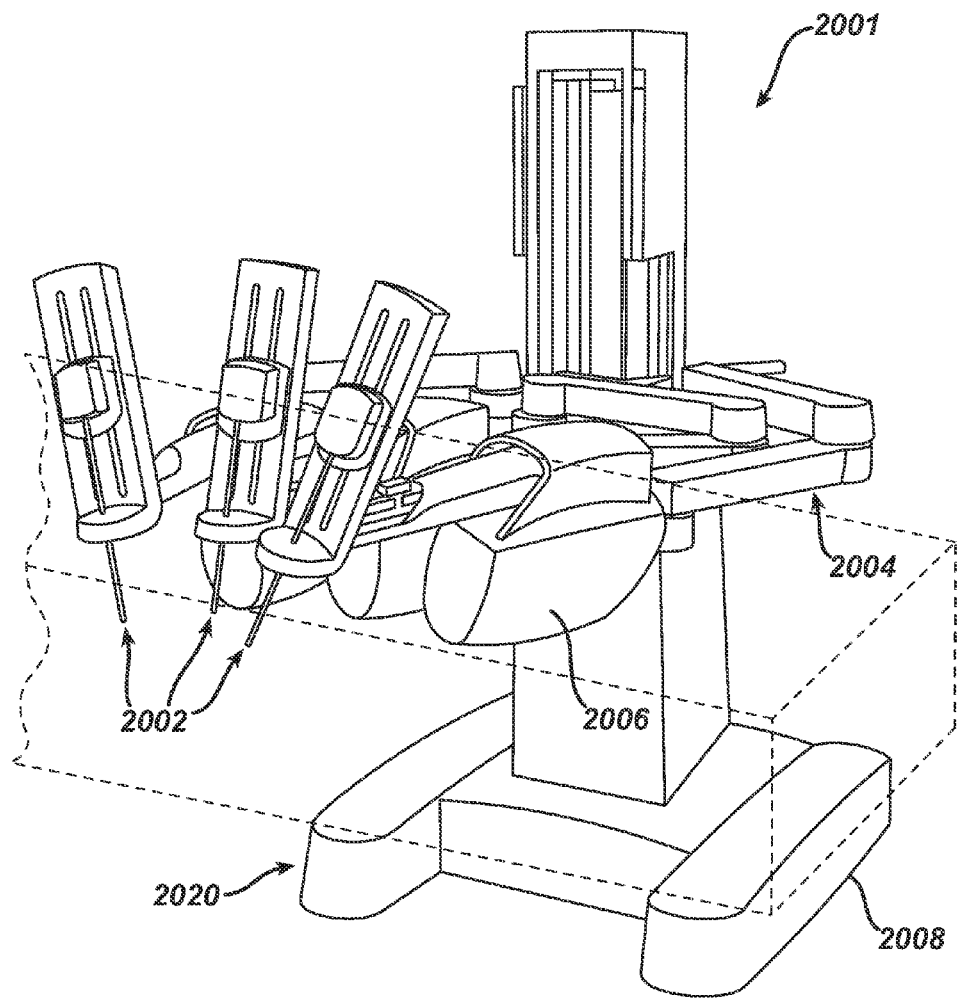
FIG. 2 is an isometric view of a robotic arm cart.

FIG. 1 depicts one version of a master controller 1001 that may be used in connection with a robotic arm slave cart 2001 of the type depicted in FIG. 2. Master controller 1001 and robotic arm slave cart 2001, as well as their respective components and control systems are collectively referred to herein as a robotic system 1000. Examples of such systems and devices are disclosed in U.S. Pat. No. 7,524,320 which has been herein incorporated by reference. Thus, various details of such devices will not be described in detail herein beyond that which may be necessary to understand various embodiments and forms of the present invention. As is known, the master controller 1001 generally includes controllers (generally represented as 1003 in FIG. 1) which are grasped by the surgeon and manipulated in space while the surgeon views the procedure via a stereo display 1002. The master controllers 1001 generally comprise manual input devices which preferably move with multiple degrees of freedom, and which often further have an actuatable handle for actuating tools (for example, for closing grasping instruments, applying an electrical potential to an electrode, or the like).

As can be seen in FIG. 2, in one form, the robotic arm cart 2001 is configured to actuate a plurality of surgical tools, generally designated as 2002. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 2001 includes a base 2008 from which, in the illustrated embodiment, three surgical tools 2002 are supported. In various forms, the surgical tools 2002 are each supported by a series of manually articulatable linkages, generally referred to as set-up joints 2004, and a robotic manipulator 2006. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 2001. Cart 2001 will generally have dimensions suitable for transporting the cart 2001 between operating rooms. The cart 2001 may be configured to typically fit through standard operating room doors and onto standard hospital elevators. In various forms, the cart 2001 would preferably have a weight and include a wheel (or other transportation) system that allows the cart 2001 to be positioned adjacent an operating table by a single attendant.

Figure 3:
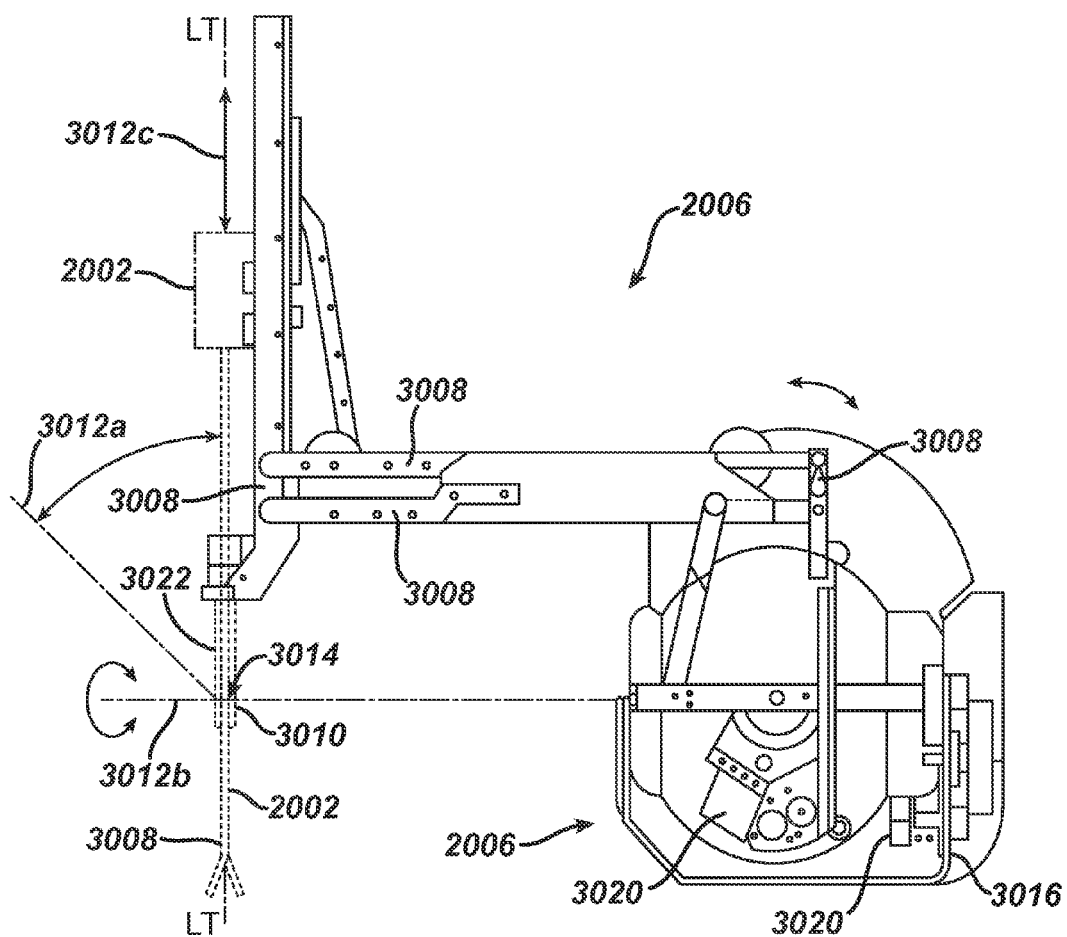
FIG. 3 is a cross-sectional view of a robotic arm assembly.

Referring now to FIG. 3, in at least one form, robotic manipulators 2006 may include a linkage 3008 that constrains movement of the surgical tool 2002. In various embodiments, linkage 3008 includes rigid links coupled together by rotational joints in a parallelogram arrangement so that the surgical tool 2002 rotates around a point in space 3010, as more fully described in issued U.S. Pat. No. 5,817,084, the full disclosure of which is herein incorporated by reference. The parallelogram arrangement constrains rotation to pivoting about an axis 3012a, sometimes called the pitch axis. The links supporting the parallelogram linkage are pivotally mounted to set-up joints 2004 (FIG. 2) so that the surgical tool 2002 further rotates about an axis 3012b, sometimes called the yaw axis. The pitch and yaw axes 3012a, 3012b intersect at the remote center 3014, which is aligned along a shaft 3008 of the surgical tool 12002. The surgical tool 2002 may have further degrees of driven freedom as supported by manipulator 2006, including sliding motion of the surgical tool 2002 along the longitudinal tool axis "LT-LT". As the surgical tool 2002 slides along the tool axis LT-LT relative to manipulator 2006 (arrow 3012c), remote center 3014 remains fixed relative to base 3016 of manipulator 2006. Hence, the entire manipulator is generally moved to re-position remote center 3014. Linkage 3008 of manipulator 2006 is driven by a series of motors 3020. These motors actively move linkage 3008 in response to commands from a processor of a control system. As will be discussed in further detail below, motors 3020 are also employed to manipulate the surgical tool 2002.

Figure 4:
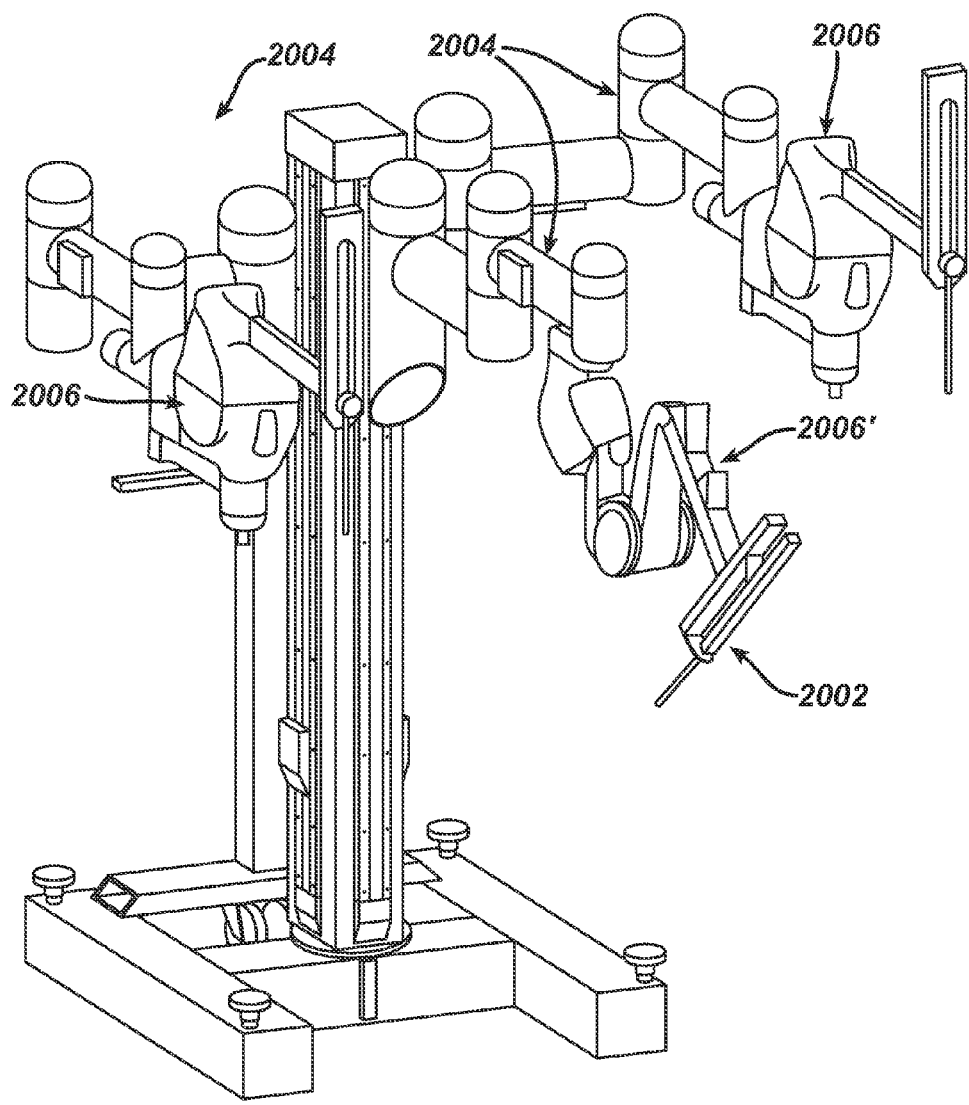
FIG. 4 is an isometric view of an alternative robotic arm cart.

An alternative set-up joint structure is illustrated in FIG. 4. In this embodiment, a surgical tool 2002 is supported by an alternative manipulator structure 2006' between two tissue manipulation tools. Those of ordinary skill in the art will appreciate that various embodiments of the present invention may incorporate a wide variety of alternative robotic structures, including those described in U.S. Pat. No. 5,878,193, entitled "Automated Endoscope System For Optimal Positioning", the full disclosure of which is incorporated herein by reference. Additionally, while the data communication between a robotic component and the processor of the robotic surgical system is primarily described herein with reference to communication between the surgical tool 2002 and the master controller 1001, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 5:
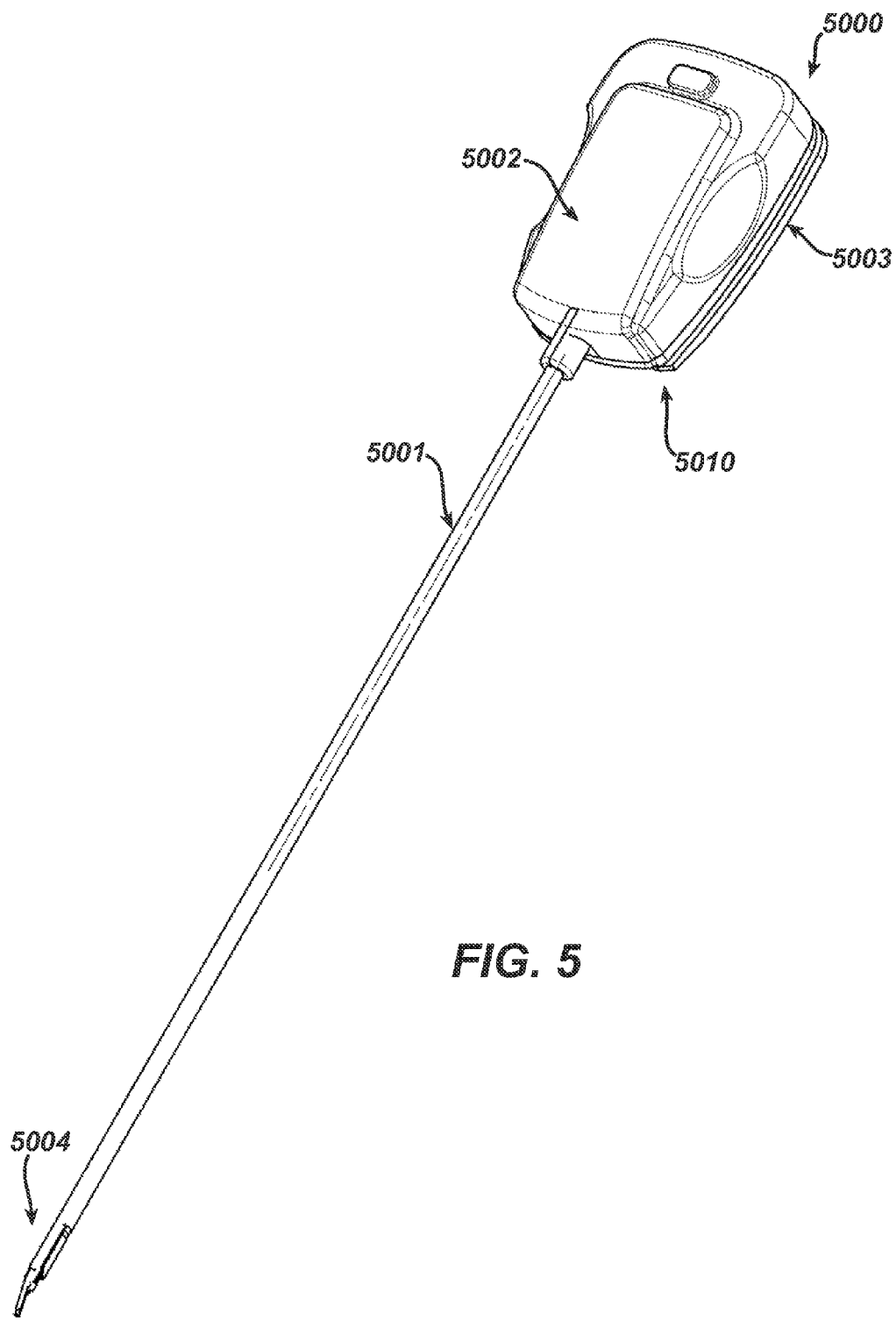
FIG. 5 is a top isometric view of a surgical tool drive assembly adapted for use with a robotic surgical system.
Figure 6:
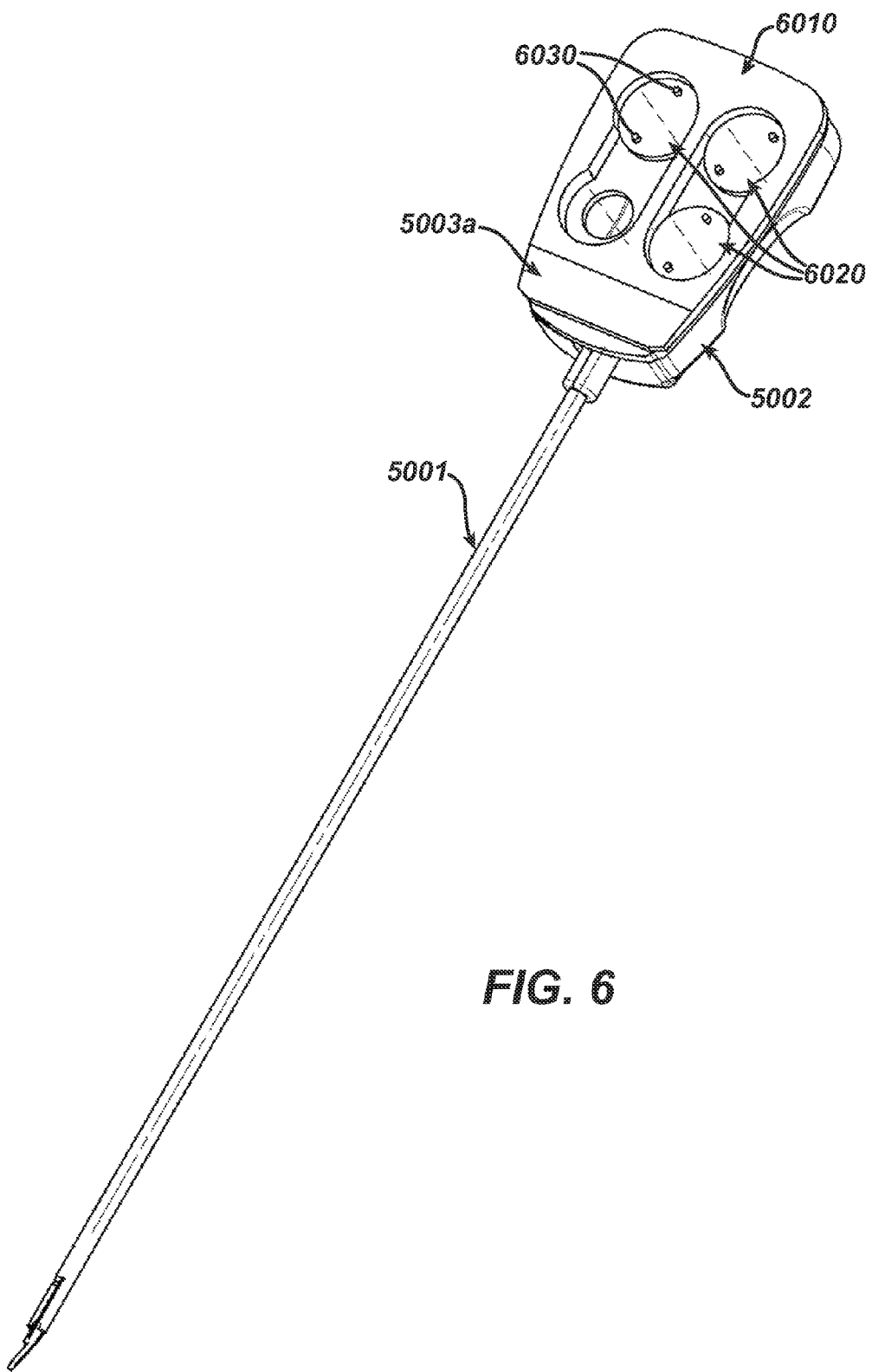
FIG. 6 is a bottom isometric view of a surgical tool drive assembly adapted for use with a robotic surgical system.

An exemplary non-limiting surgical tool 2002 that is well-adapted for use with a robotic system 1000 that has a tool drive assembly 5000 that is operatively coupled to a master controller 1001 that is operable by inputs from an operator (i.e., a surgeon) is depicted in FIG. 5. As can be seen in that Figure, the surgical tool 5000 includes a surgical end effector 5004 that comprises a clip applier. In at least one form, the surgical tool 5000 generally includes an elongated shaft assembly 5001 that has a distal jaw assembly 5004. The surgical tool 5000 is operably coupled to the manipulator by a tool mounting portion, generally designated as 5003. The surgical tool 5000 further includes an interface 6010 (see FIG. 6) which mechanically and electrically couples the tool mounting portion 5003 to the manipulator. In various embodiments, the tool mounting portion 5003 includes a tool mounting plate 5003a that operably supports a plurality of (four are shown in FIG. 6) rotatable body portions, driven discs or elements 6020, that each include a pair of pins 6030 that extend from a surface of the driven element 6020. One pin 6030 may be closer to an axis of rotation of each driven elements 6020 than the other pin 6030 on the same driven element 6020, which may help to ensure positive angular alignment of the driven element 6020. Interface 6010 is adapted to engage a mounting surface on arm 2006. The mounting portion 5003 may include an array of electrical connecting pins (not shown) which may be coupled to an electrical connection on arm 2006, as is known and understood in the art. While interface 5003 is described herein with reference to mechanical, electrical, and magnetic coupling elements, it should be understood that a wide variety of telemetry modalities might be used, including infrared, inductive coupling, or the like.

Figure 7:
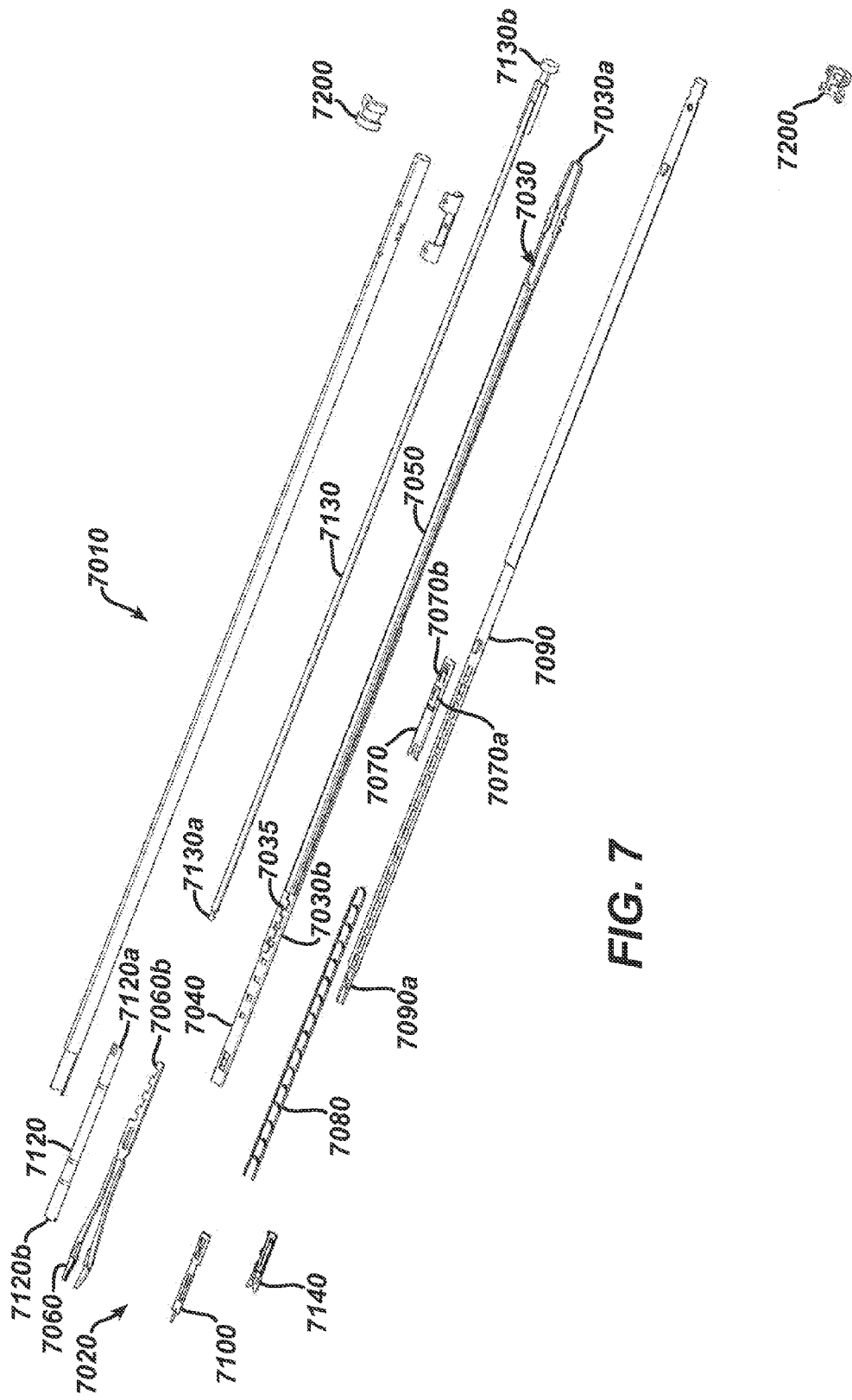
FIG. 7 is an exploded view of a clip applier shaft adapted for use with a surgical tool drive assembly.

FIG. 7 illustrates an exploded view of one exemplary surgical clip applier shaft 5001 and jaw assembly 5004. Such clip applier assemblies have previously been described in U.S. Pat. No. 7,261,724 entitled "Surgical Clip Advancement Mechanism", U.S. Pat. No. 7,288,098 entitled "Force Limiting Mechanism For Medical Instrument", U.S. Pat. No. 7,297,149 entitled "Surgical Clip Applier Methods", U.S. Pat. No. 7,686,820 entitled "Surgical Clip Applier Ratchet Mechanism", U.S. Pat. No. 7,699,860 entitled "Surgical Clip", and U.S. Pat. No. 7,731,724 entitled "Surgical Clip Advancement and Alignment Mechanism" the entire contents of which are herein incorporated by reference. The various components will be described in more detail below.

The shaft 5001 includes an outer tube 7010 that houses the shaft components, which can include a jaw retaining assembly 7020 having a jaw retainer shaft 7030 with a clip track 7040 and a push rod channel 7050 formed thereon. The jaws 7060 can be configured to mate to a distal end of the clip track 7040. The shaft assembly 5001 can also include a clip advancing assembly, which in one exemplary embodiment can include a feeder shoe 7070 that is adapted to be slidably disposed within the clip track 7040 to advance a series of clips 7080 positioned therein, and a feed bar 7090 that is adapted to drive the feeder shoe 7070 through the clip track 7040. The feed bar 7090 can include an advancer assembly 7100 that is adapted to mate to a distal end thereof for advancing a distalmost clip into the jaws 7060. The shaft assembly 5001 can also include a clip forming or camming assembly, which in one exemplary embodiment can include a cam 7120 that is adapted to slidably mate to the jaws 7060, and a push rod 7130 that can couple to the cam 7120 to move the cam 7120 relative to the jaws 7060. The shaft assembly can also include a tissue stop 7140 that can mate to a distal end of the clip track 7040 for facilitating positioning of the jaws 7060 relative to a surgical site.

Referring still to FIG. 7, the jaw retaining assembly 7020 is shown and it includes an elongate, substantially planar jaw retainer shaft 7030 having a proximal end 7030*a* that mates to the outer tube 7010, and a distal end 7030*b* that is adapted to mate to the jaws 7060. While a variety of techniques can be used to mate the proximal end 7030*a* of the jaw retainer shaft 7030 to the outer tube 7010, in the illustrated embodiment the proximal end 7030*a* includes teeth 7035 formed on opposed sides thereof that are adapted to be received within corresponding holes or openings (not shown) formed in the outer tube 7010, and a cut-out 7036 formed therein that allows the opposed sides of the proximal end 7030*a* to deflect or to form a spring. In particular, the cut-out 7036 allows the opposed sides of the proximal end 7030*a* of the jaw retainer shaft 7030 to be compressed toward one another when the jaw retainer shaft 7030 is inserted in the outer tube 7010. Once the teeth 7035 are aligned with the corresponding openings in the outer tube 7010, the proximal end 7030*a* of the jaw retainer shaft 7030 will return to its original, uncompressed configuration thereby causing the teeth 7035 to extend into the corresponding openings to engage the outer tube 7010.

A variety of techniques can also be used to mate the distal end 7030*b* of the jaw retainer shaft 7030 to the jaws 7060, however in the illustrated embodiment the distal end 7030*b* of the jaw retainer shaft 7030 includes several cut-outs or teeth 7035 formed therein for mating with corresponding protrusions or teeth 7060*b* formed on the jaws 7060. The teeth 7035 allow a proximal portion of the jaws 7060 to be substantially co-planar with the jaw retainer shaft 7030.

The jaw retaining assembly 7020 can also include a push rod channel 7050 formed thereon for slidably receiving the push rod 7130, which is used to advanced the cam 7120 over the jaws 7060. The push rod channel 7050 can be formed using a variety of techniques, and it can have any shape and size depending on the shape and size of the push rod 7130. As shown, the push rod channel 7050 is fixedly attached, e.g., by welding, to a superior surface of the retainer shaft 7030, and it has a substantially rectangular shape and defines a pathway extending therethrough. The push rod channel 7050 can also extend along all or only a portion of the retainer shaft 7030. A person skilled in the art will appreciate that the jaw retaining assembly 7020 does not need to include a push rod channel 7050 for facilitating movement of the push rod 7130 within the elongate shaft 5001 of the surgical clip applier 5000.

The jaw retaining assembly 7020 can also include a clip track 7040 mated thereto or formed thereon. The clip track 7040 is mated to an inferior surface of the jaw retainer shaft 7030, and it extends distally beyond the distal end 7030*b* of the jaw retainer shaft 7030 to allow a distal end of the clip track 7040 to be substantially aligned with the jaws 7060. In use, the clip track 7040 is configured to seat at least one, and preferably a series, of clips therein. Accordingly, the clip track 7040 can include opposed side rails that are adapted to seat opposed legs of one or more clips therein, such that the legs of the clips are axially aligned with one another. In an exemplary embodiment, the clip track 7040 can be configured to seat about twenty clips that are pre-disposed within the clip track 7040 during manufacturing. A person skilled in the art will appreciate that the shape, size, and configuration of the clip track 7040 can vary depending on the shape, size, number and configuration of clips, or other closure devices such as staples, adapted to be received therein. Moreover, a variety of other techniques can be used, instead of a clip track 7040, to retain a clip supply with the elongate shaft 5001.

The clip track 7040 can also include several openings formed therein for receiving a tang 7070*a* formed on a feeder shoe 7070 adapted to be disposed within the clip track 7040. In an exemplary embodiment, the clip track 7040 includes a quantity of openings that corresponds to at least the number of clips adapted to be pre-disposed within the device 5000 and applied during use. The openings are preferably equidistant from one another to ensure that the tang 7070*a* on the feeder shoe 7070 engages an opening each time the feeder shoe 7070 is advanced. While not shown, the clip track 7040 can include detents, rather than openings, or it can include other features that allow the clip track 7040 to engage the feeder shoe 7070 and prevent distal movement, yet allow proximal movement, of the feeder shoe 7070. The clip track 7040 can also include a stop tang formed thereon that is effective to be engaged by a corresponding stop tang formed on the feeder shoe 7070 to prevent movement of the feeder shoe 7070 beyond a distalmost position. The stop tang can have a variety of configurations, but in one exemplary embodiment it is in the form of two adjacent tabs that extend toward one another to enclose a portion of the clip track, thus allowing clips to pass therethrough.

To facilitate proximal movement of the feeder shoe 7070 within the clip track 7040, the feeder shoe 7070 can also include a tang 7070*b* formed on the inferior surface thereof for allowing the feeder shoe 7070 to be engaged by the feed bar 7090 as the feed bar 7090 is moved distally. The inferior tang 7070*b* is similar to the superior tang 7070*a* in that it can be angled proximally. In use, each time the feed bar 7090 is moved distally, a detent formed in the feed bar 7090 can engage the inferior tang 7070*b* and move the feeder shoe 7070 distally a predetermined distance within the clip track 7040. The feed bar 7090 can then be moved proximally to return to its initial position, and the angle of the inferior tang 7070*b* will allow the tang to slide into the next detent formed in the feed bar 7090. A variety of other features rather than tangs and openings or detents can be used to control movement of the feeder shoe 7070 within the clip track 7040.

As previously mentioned, the feeder shoe 7070 can also include a stop formed thereon that is adapted to stop movement of the feeder shoe 7070 when the feeder shoe 7070 is in the distal-most position and there are no clips remaining in the device 5000. While the stop can have a variety of configurations, a third tang may be formed on the feeder shoe 7070 and extending in an inferior direction for engaging a stop tang formed on the clip track 7040, as is known and understood in the art. The third tang is positioned such that it will engage the stop tang 7090a on the clip track 7040 when the feeder shoe 7070 is in a distal-most position, thereby preventing movement of the feeder shoe 7070 and the feed bar 7090 when the clip supply is depleted.

As shown, the feed bar 7090 has a generally elongate shape with proximal and distal ends. The proximal end of the feed bar 7090 can be adapted to mate to a feed bar coupler 7200. The feed bar coupler 7200 can mate to a variety of feed links that are effective, upon actuation, to slidably move the feed bar 7090 in a distal direction within the elongate shaft 5001, 7010 thereby advancing a clip into the jaws 7060.

Still referring to FIG. 7, an exemplary embodiment of the jaws 7060 are shown. As previously mentioned, the jaws 7060 can include a proximal portion having teeth 7060b for mating with corresponding teeth 7035 formed on the jaw retaining shaft 7030. Other techniques can, however, be used to mate the jaws 7060 to the jaw retaining shaft 7030. For example, a dovetail connection, a male-female connection, etc., can be used. Alternatively, the jaws 7060 can be integrally formed with the retaining shaft 7030. The distal portion of the jaws 7060 can be adapted to receive a clip therebetween, and thus the distal portion can include first and second opposed jaw members that are movable relative to one another. In an exemplary embodiment, the jaw members are biased to an open position, and a force is required to move the jaw members toward one another. The jaw members can each include a groove formed therein on opposed inner surfaces thereof for receiving the legs of a clip in alignment with the jaw members. The jaws members can also each include a cam track formed therein for allowing the cam 7120 to engage the jaw members and move the jaw members toward one another. In an exemplary embodiment, the cam track is formed on a superior surface of the jaw members.

An exemplary cam 7120 for slidably mating to and engaging the jaw members is depicted in FIG. 7. The cam 7120 can have a variety of configurations, but in the illustrated embodiment it includes a proximal end 7120a that is adapted to mate to a push rod 7130, and a distal end adapted to engage the jaw members. A variety of techniques can be used to mate the cam 7120 to the push rod 7130, but in the illustrated exemplary embodiment the cam 7120 includes a female or keyed cut-out formed therein and adapted to receive a male or key member 7130a formed on the distal end of the push rod 7130. As shown, the male member 7130a has a shape that corresponds to the shape of the cut-out to allow the two members 7120, 7130 to mate. A person skilled in the art will appreciate that the cam 7120 and the push rod 7130 can optionally be integrally formed with one another. The proximal end 7130b of the push rod 7130 can be adapted to mate to a closure link assembly, for moving the push rod 7130 and the cam 7120 relative to the jaws 7060.

While a variety of techniques can be used, in the illustrated exemplary embodiment the distal end 7120b includes a camming channel or tapering recess formed therein for slidably receiving the cam tracks on the jaw members. In use, the cam 7120 can be advanced from a proximal position, in which the jaw members are spaced a distance apart from one another, to a distal position, in which the jaw members are positioned adjacent to one another and in a closed position. As the cam 7120 is advanced over the jaw members the tapering recess will push the jaw members toward one another, thereby crimping a clip disposed therebetween.

Figure 8:
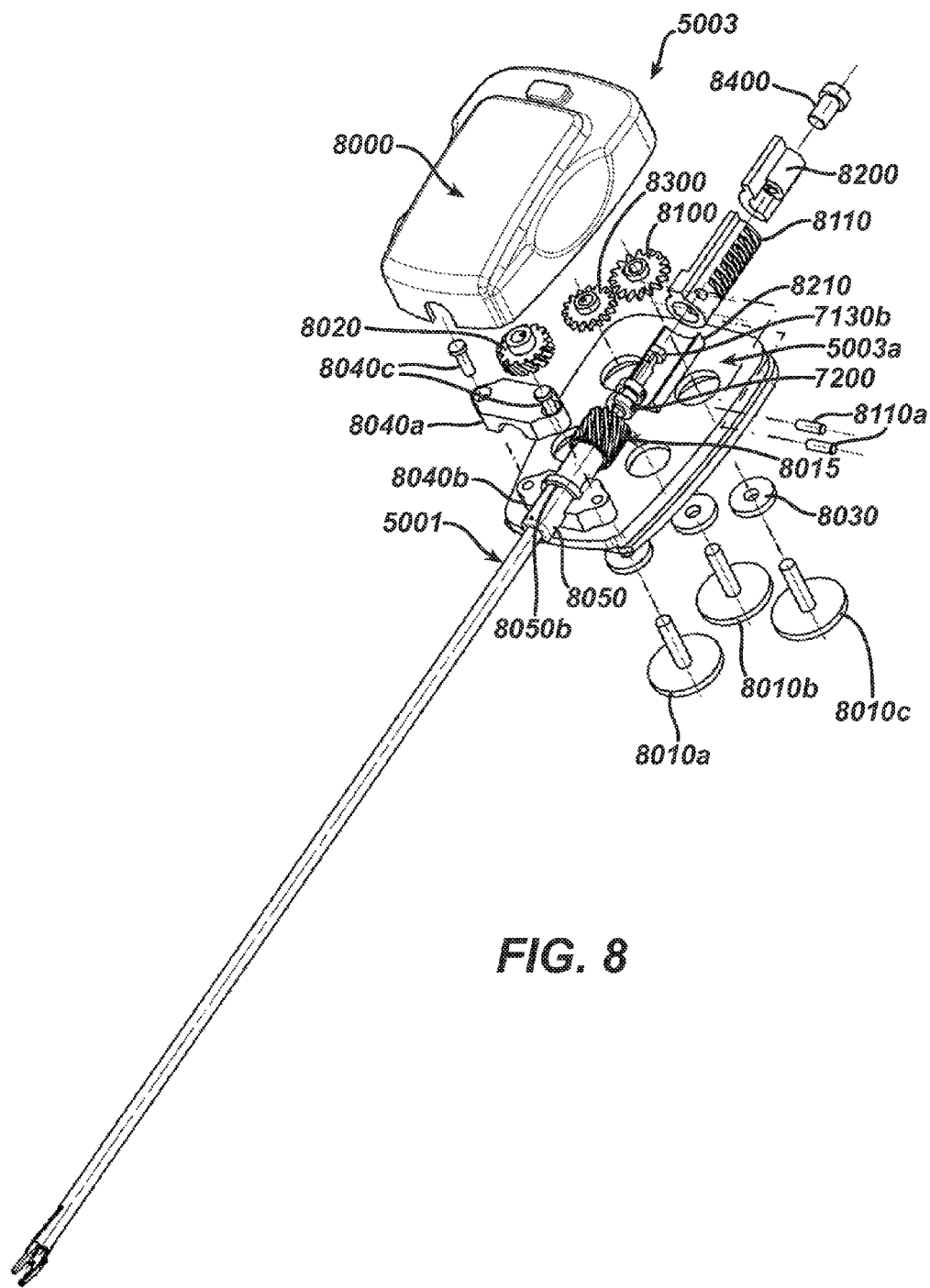
FIG. 8 is an exploded view of a first expression of a surgical tool drive assembly adapted for use with a robotic surgical system.

Referring now to FIG. 8, an exploded view of one expression of clip applier 5000 is shown. In this expression, the clip applier 5000 includes rotatable bodies or spools 8010a, 8010b, 8010c and are coupled to rotatable bodies or drive elements 6020. The spools 8010a,b,c may be formed integrally with the driven elements 6020. In other expressions, spools may be formed separately from the driven elements 6020 provided that the spools 8010a,b,c and the elements 6020 are fixedly coupled such that driving the elements 6020 causes rotation of the spools 8010a,b,c. Each spool 8010a,b,c is coupled to a gear train or drive assembly for translating motion to the shaft 7010 (or outer tube) for rotating the shaft, advancing a clip and forming a clip. As shown, spools 8010a,b,c interface with spool bearings 8030 seated between spools 8010a,b,c and mounting plate 5003a to facilitate smooth transfer of rotational forced from corresponding drive elements on the robotic arm 2006. The bearings 8030 may further be provided to support and stabilize the mounting of spools 8010a,b,c and reduce rotary friction of shaft and gears, for example.

Figure 9A:
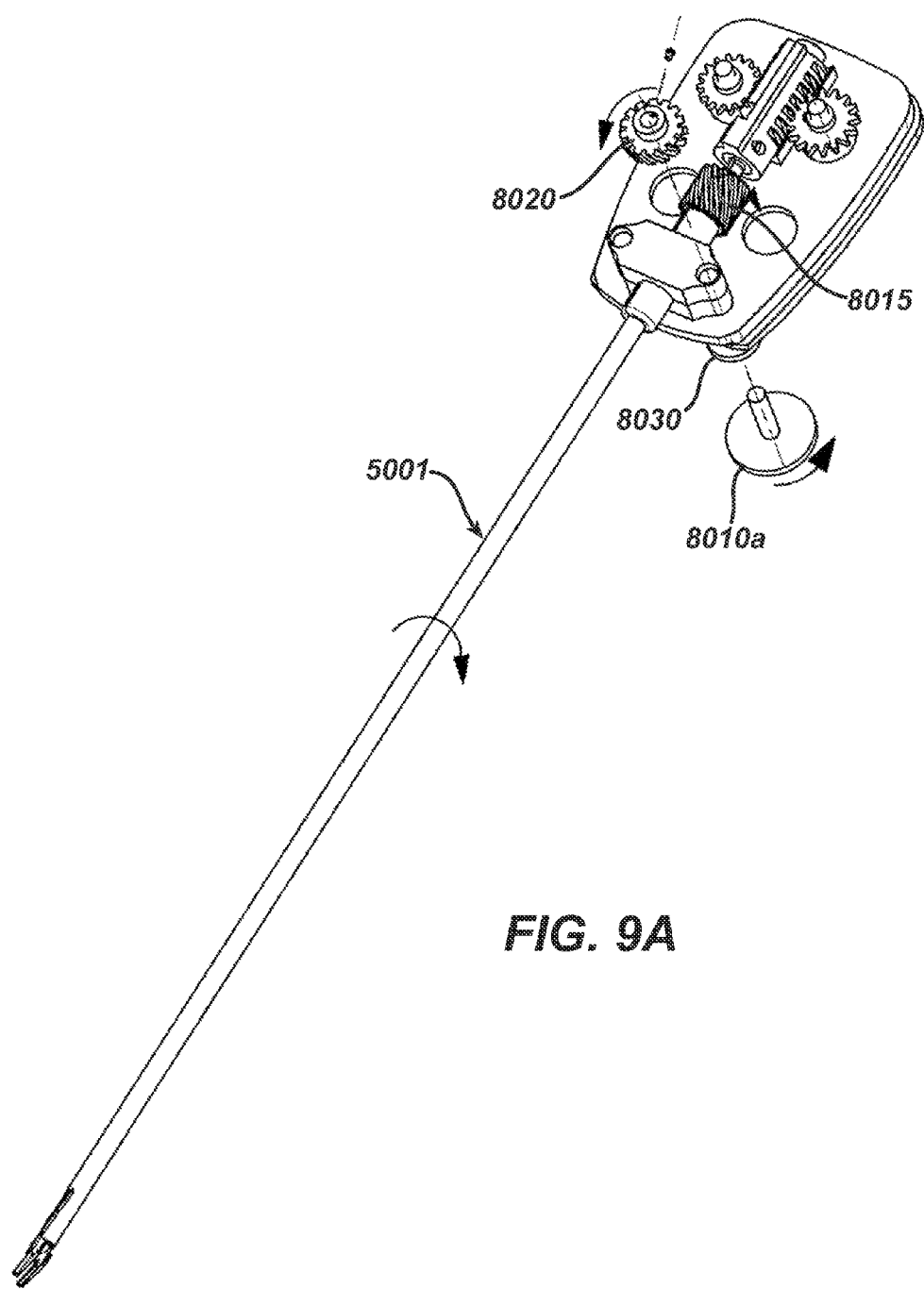
FIG. 9A is an assembly view of the FIG. 8 expression rotation mechanism.
Figure 9B:
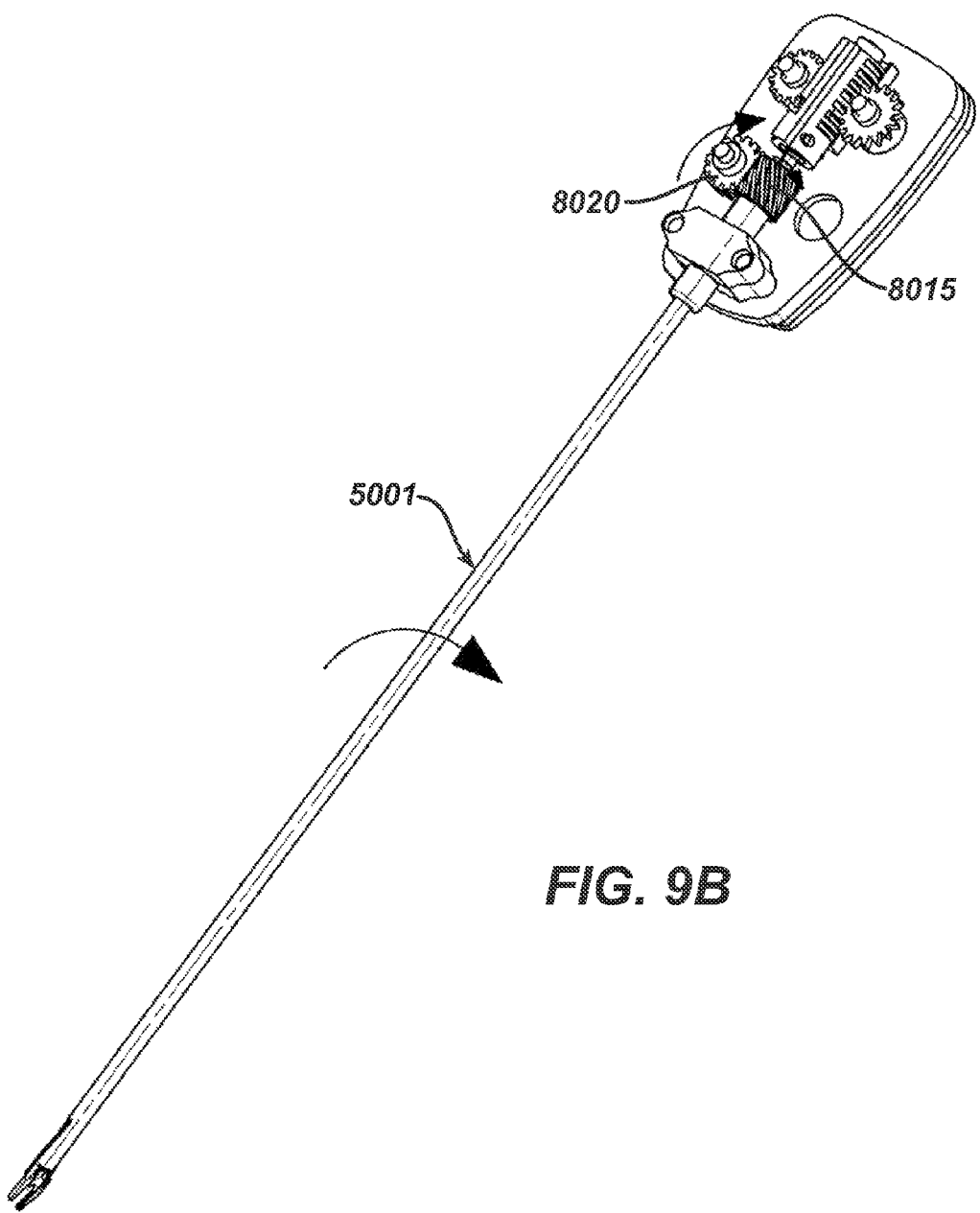
FIG. 9B is an isometric view of the FIG. 8 rotation mechanism in operation.

In the FIG. 8 expression, the tool mounting portion 5003 of the clip applier 5000 comprises a shaft assembly rotation mechanism. In the illustrated expression, for example, the surgical tool 5000 comprises a first spiral worm gear 8020 coupled to a rotatable body 6020 and a second spiral worm gear 8015 coupled to the shaft assembly 5001. A bearing 8030 is coupled to a spool 8010a and is provided between a driven element 8010a and the mounting plate 6010. The first spiral worm gear 8020 is meshed to the second spiral worm gear 8015, which is coupled to the shaft assembly 5001, to control the rotation of the shaft assembly 5001 in a clockwise (CW) and counter-clockwise (CCW) direction based on the rotational direction of the first and second spiral worm gears 8015 and 8020. Accordingly, rotation of the first spiral worm gear 8020 about a first axis is converted to rotation of the second spiral worm gear 8015 about a second axis, which is orthogonal to the first axis. As shown in FIGS. 9A and 9B, for example, a CCW rotation of the spool 8010a results in the first spiral worm gear 8020 rotating in a CCW direction which in turn rotates the shaft assembly 5001 in the direction indicated in FIG. 9A which is CW. It is appreciated that the spool may be rotated incrementally to provide precise rotation of the shaft. Such precise rotation may be enabled by an electrical interface between the user console 1000 and clip applier 5000 driven by a software algorithm, as is known and understood in the art. Shaft 5001 may be rotatably fixed to mounting assembly 5010 by means of bearing clamp 8040, comprised of clamp halves 8040a and 8040b. Shaft 5001 is provided with a shaft collar 8050 that is fixedly attached to shaft 5001 and worm gear 8015 that permits transfer of rotational force from worm gear 8015 to shaft 5001. Clamp halves 8040a and 8040b act as a bearing and enclose shaft collar 8050 and are provided with recesses to permit free rotation of shaft 5001 while prohibiting shaft 5001 linear motion. In the present expression, clamp collar 8050 is a provided with an annular flange 8050b to mate with clamp 8040 recesses prevent axial motion.

Still referring to the FIG. 8 expression, tool mounting portion 5003 of clip applier 5010 comprises a clip feed mechanism to feed clips into jaws 7060. In the illustrated expression for example, the surgical tool 5000 comprises a rack and pinion gearing mechanism to provide the clip feed functionality. A feeding gear 8100 is coupled to a spool 8010c such that rotation of the corresponding driven element 6020 causes the spool 8010c and feed gear 8100 to rotate in a first direction. In the FIG. 8 expression, the feed gear 8100 is a pinion gear meshed to a feed rack gear 8110, which moves in a linear direction. The rack gear 8110 is coupled to feedbar coupler 7200 by pins 8110a, which is fixedly attached to feedbar 7030, as was described above. As shown, feeding rack 8110 is provided with a cut-out portion configured to nestle with a similar cut-out portion on forming rack 8200 such that the feeding and forming rack together encircle shaft 5001, have a contiguous outer diameter, yet move independent of one-another. Feed rack 8110 is configured with an annular portion where a portion of the annular outer surfaces comprises the rack teeth. The feed rack 8110 further comprises a flange portion adapted to slideably mate with a similar flange on forming rack 8200. Tool mounting portion is further provided with a rack slide 8210, and rack channel (not shown) located in cover 8000 adapted to receive feed rack 8110 and form rack 8200 flanges together and adapted to hold feeding rack 8110 and forming rack 8200 in a fixed rotational position relative to tool mounting portion 5003 while permitting linear movement.

Figure 10A:
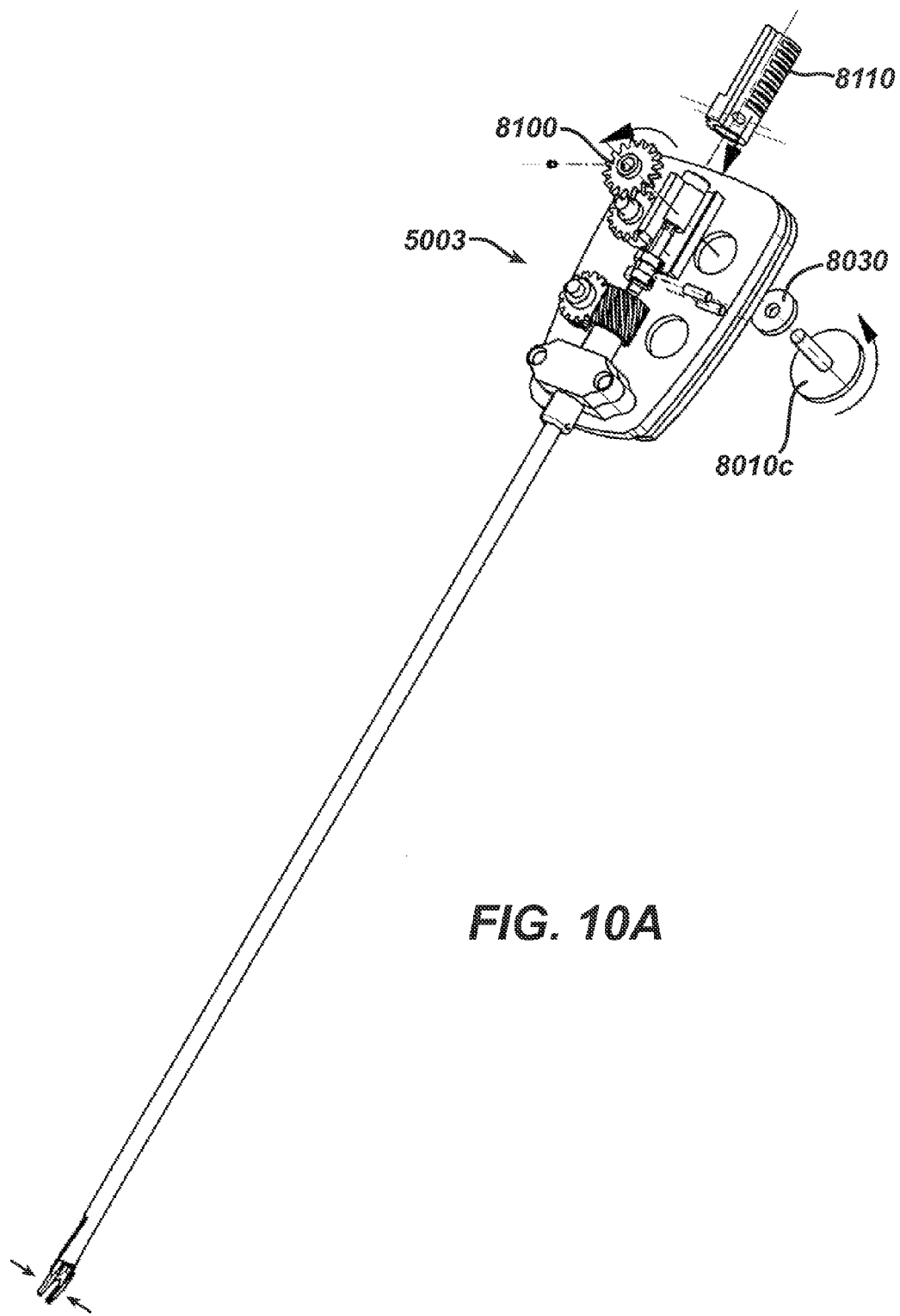
FIG. 10A is an assembly view of the FIG. 8 expression clip feed mechanism
Figure 10B:
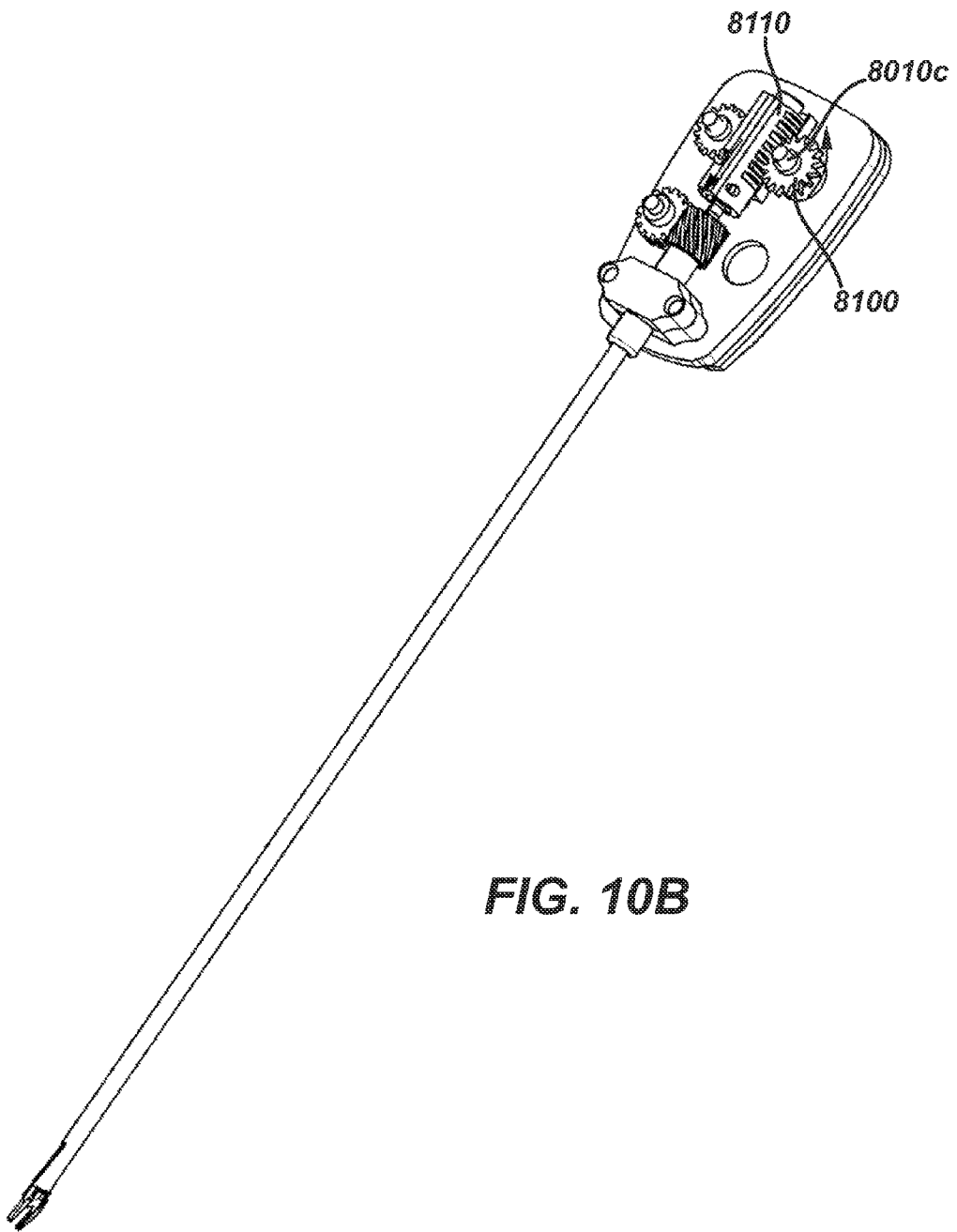
FIG. 10B is an isometric view of the FIG. 8 clip feeding mechanism in operation

In operation, referring to FIGS. 10A and 10B, the feed pinion 8100 is meshed with feed rack 8110 in tool mounting portion 5003. Feed spool 8010c is rotated in a CCW direction which in turn rotates feed pinion 8100 in a counter-clockwise direction. In the present expression, feed pinion 8100 is rotated sufficiently to advance rack 8110 distally a sufficient distance to fully advance a clip into the jaws 7060. Rack 8110 travel distance may vary based upon several factors e.g. clip leg length, jaw length. In the present expression, feed rack travels approximately 0.25 inches. Feed pinion 8100 rotation may be precisely controlled by an electrical and software interface to deliver the exact feed rack 8110 travel necessary to feed a clip into the jaws 7060. Upon delivery of a clip into the jaws or after a predetermined amount of rotation of feed pinion 8100, rotation of pinion 8100 is reversed to a CW direction to move feed rack 8110 in a proximal direction, in turn moving feedbar coupler 7200 proximally, which in turn moves feedbar 7030 proximally, as was described above. This process may be repeated several times to accommodate a predetermined number of clips residing in the shaft. The software interface may be programmed to count down the number of clips fed into the jaws and display the same to the user and may further prevent the user from attempting to feed another clip once the shaft is empty. It is contemplated that the software interface may alert the user when the shaft contains a predetermined amount of clips.

Referring back to FIG. 8, tool mounting portion 5003 of clip applier 5000 comprises a clip forming mechanism to form clips in jaws 7060. In the illustrated expression for example, the surgical tool 5000 comprises a rack and pinion gearing mechanism to provide the clip forming functionality. A forming gear 8300 is coupled to a spool 8010b such that rotation of the corresponding driven element 6020 causes the spool 8010b and forming gear 8300 to rotate in a first direction. In the FIG. 8 expression, the forming gear 8300 is a pinion gear meshed to a feed rack gear 8200, which moves in a linear direction. The rack gear 8200 is coupled to male end 7130b of pushrod 7130, as was described above and is locked in place about shaft 5001 with an assembly lock 8400. As shown, forming rack 8200 is configured to nestle with feeding rack 8110 such that the feeding and forming rack encircle shaft 5001 yet move independent of one-another. Forming rack 8200 is configured with an annular outer surface where a portion of the annular outer surfaces comprises rack teeth which are adapted to mesh with pinion gear 8300. The forming rack 8200 further comprises a flange portion adapted to slideably mate with a similar flange on forming rack 8110 as described above. Together, feed rack 8010 and form rack 8200 flanges mate with channel in cover 8000 to permit linear movement while prevents lateral or rotational motion.

Figure 11A:
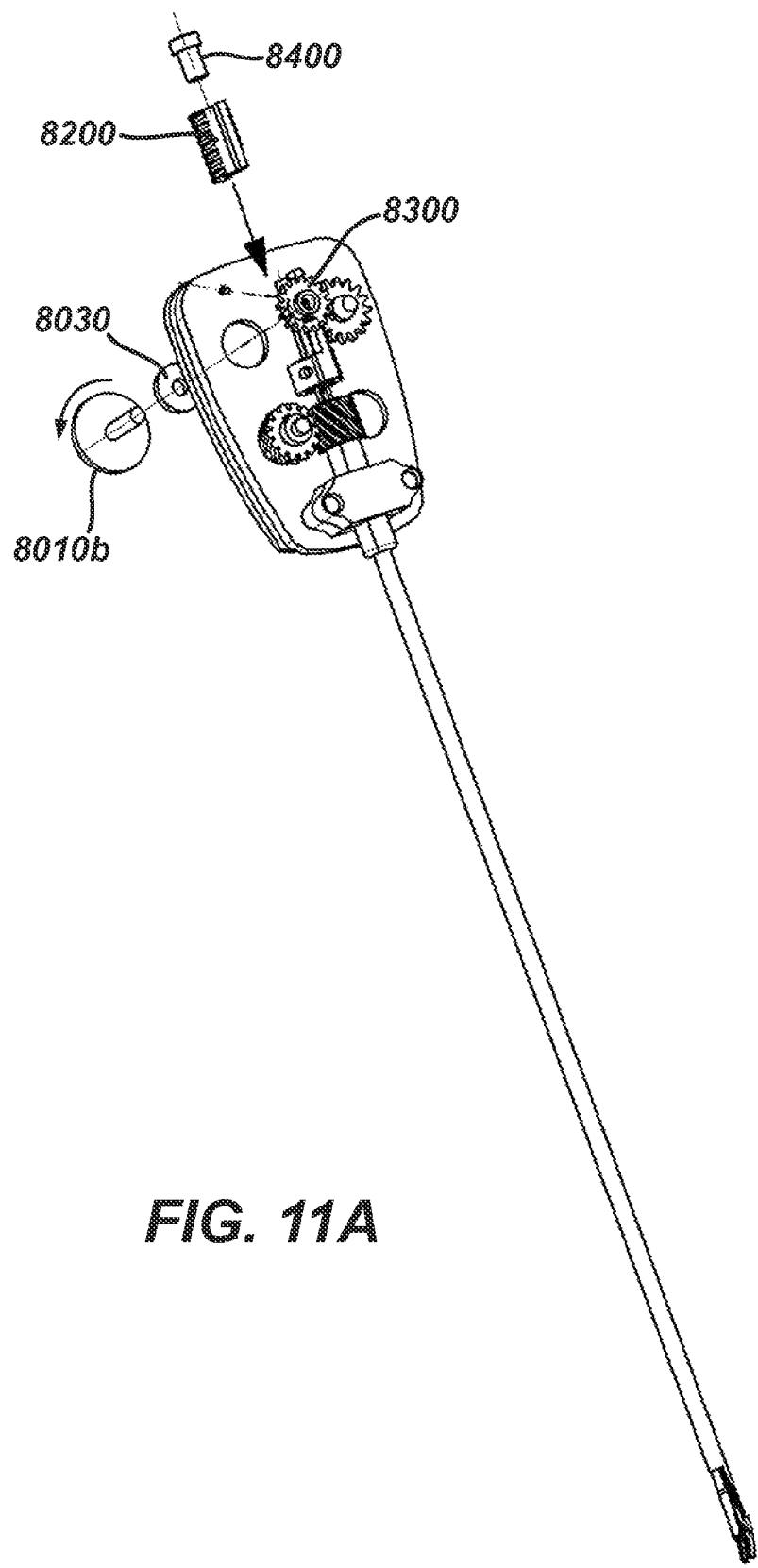
FIG. 11A is an assembly view of the FIG. 8 expression clip forming mechanism.
Figure 11B:
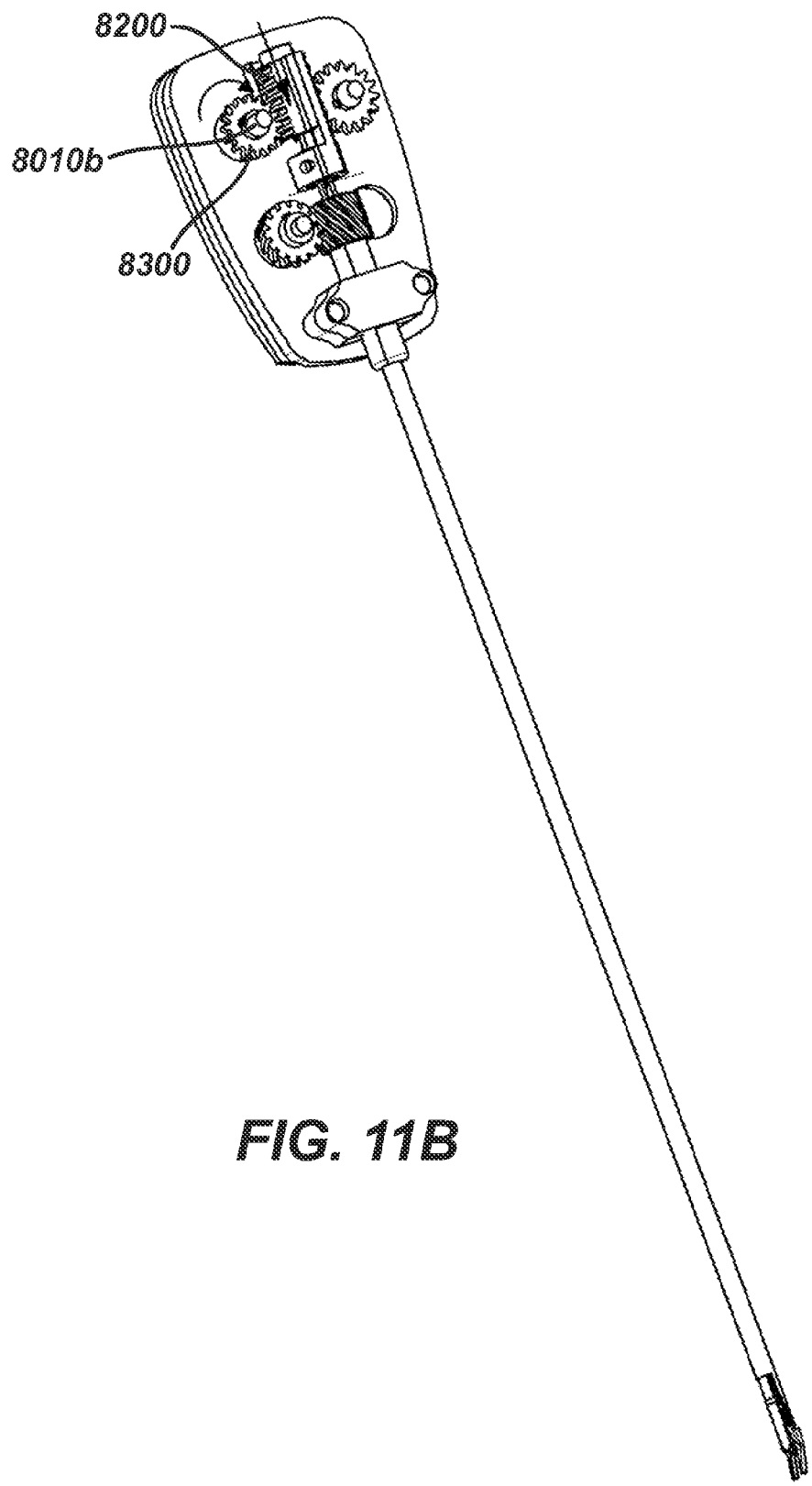
FIG. 11B is an isometric view of the FIG. 8 clip forming mechanism in operation.

In operation, referring now to FIGS. 11A and 11B, the form pinion 8300 is fixedly attached to spool 8010b and is meshed with rack 8200 in tool mounting portion 5003. Once the feed function is complete and a clip is present in jaws, spool 8010b rotates in a CW direction imparting CW rotation to pinion 8300 which in turn drives rack 8200 in a distal linear direction. Such distal linear motion of rack 8200 drives pushrod 7130 in a distal linear direction which drives cam 7120 over jaws 7060 forming or crimping a clip in jaws 7060, as was described above.

Rotation of pinion 8300 may be precisely controlled to impart a sufficient number of rotations to advance rack 8200 a predetermined distance to fully form a clip. Alternatively, pinion 8300 may be rotated slowly and stopped to permit partial formation of a clip about an anatomic structure which enables movement of the clip in a less than fully formed state about an anatomic structure. Once a clip deployment location is selected, pinion 8300 may be rotated such that a clip is fully formed, occluding an anatomic structure. Once a clip is deployed, pinion 8300 is rotated in a CCW direction, which drives rack 8200 in a proximal direction, moving pushrod 7130 proximally which drives cam 7120 proximally, permitting jaws 7060 to open. It is contemplated that jaw 7060 opening and closing may be performed independently of clip feeding, thus allowing a user to utilize clip applier 5000 jaws 7060 as a dissector.

Figure 12:
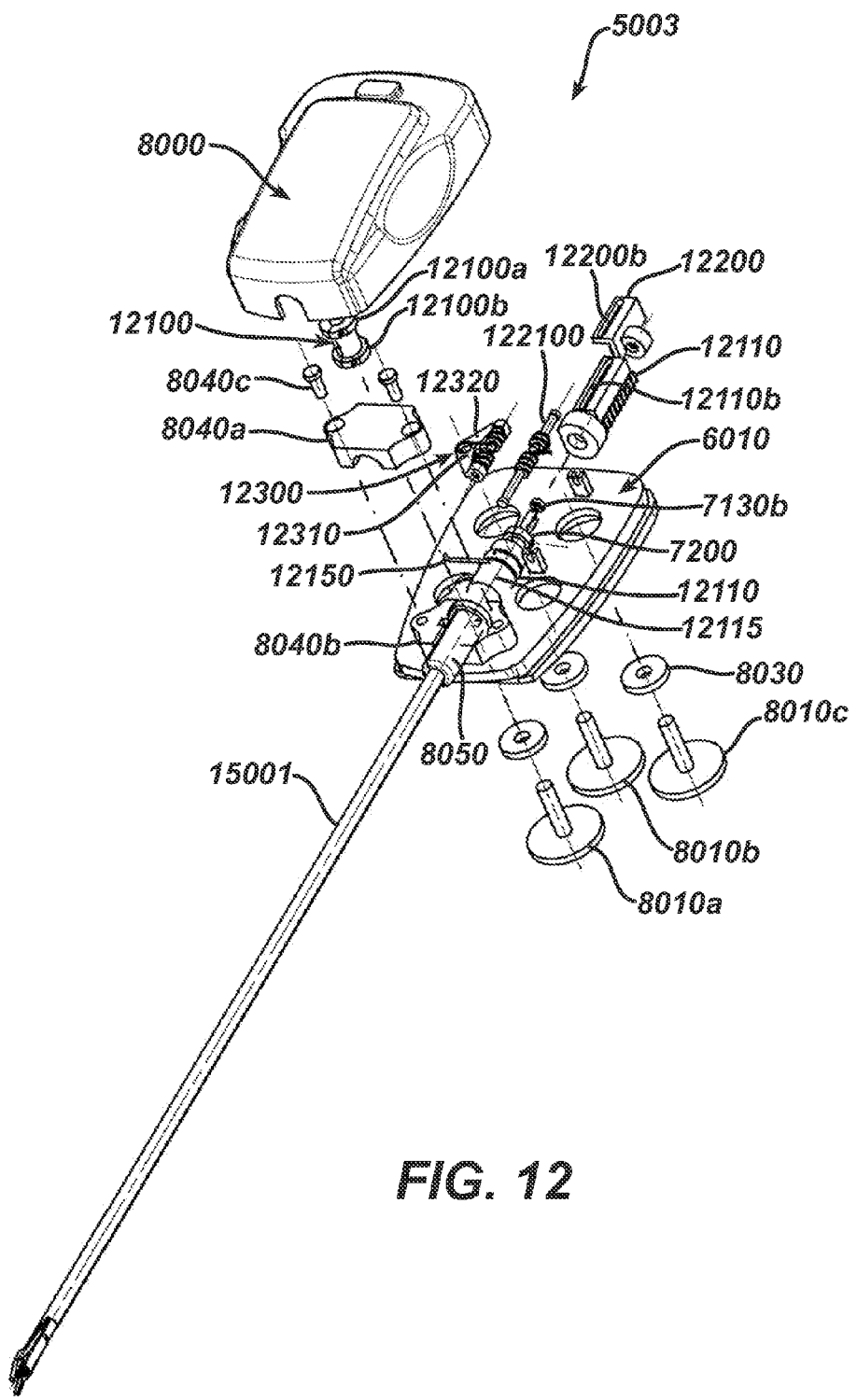
FIG. 12 is an exploded view of a second expression of a surgical tool drive assembly adapted for use with a robotic surgical system.
Figure 13A:
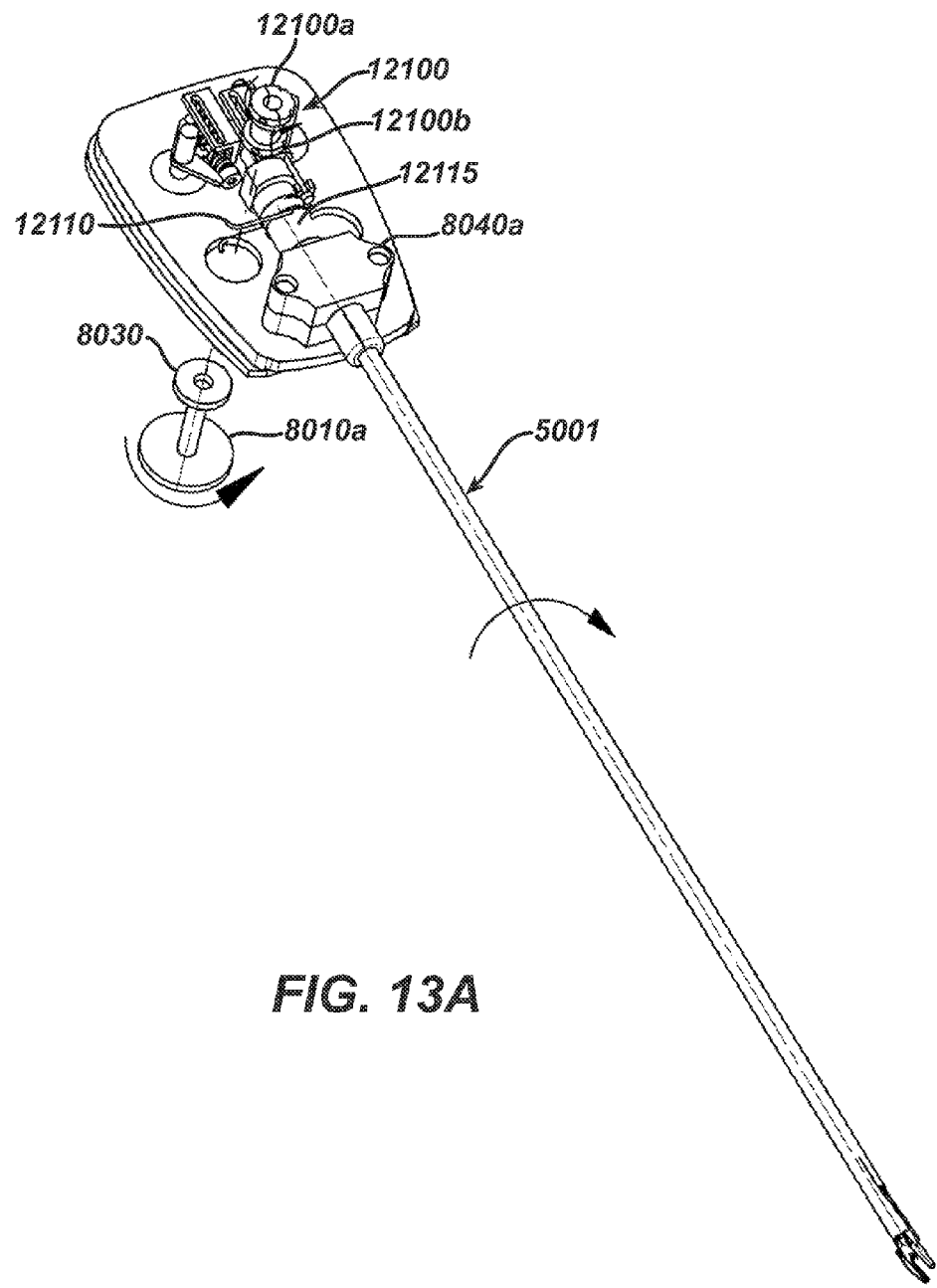
FIG. 13A is an assembly view of the FIG. 12 expression rotation mechanism.
Figure 13B:
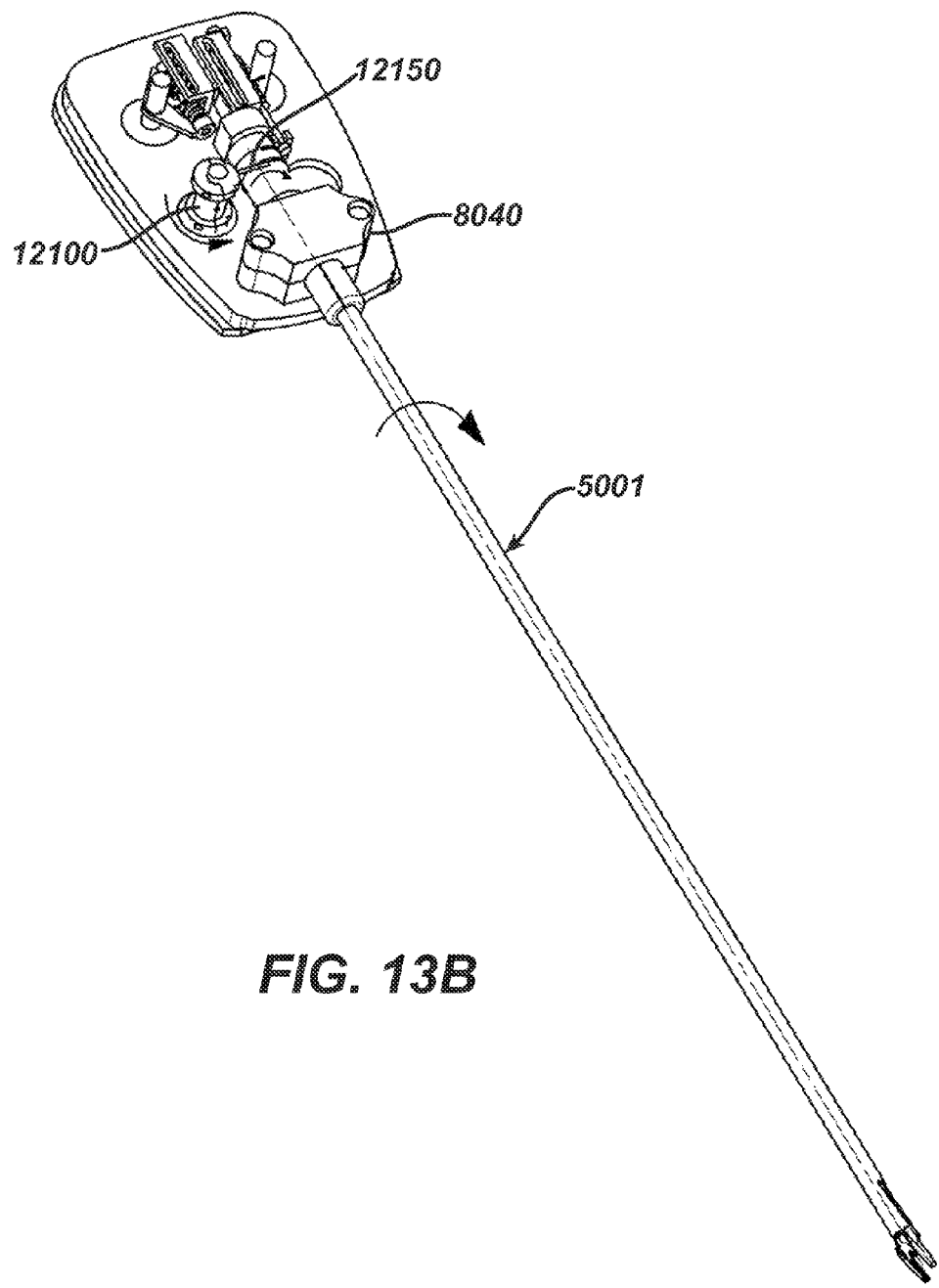
FIG. 13B is an isometric view of the FIG. 12 rotation mechanism in operation.

Referring now to FIG. 12, a second expression of clip applier 5000 is shown. In the FIG. 12 expression, the tool mounting portion 5003 of the clip applier 5000 comprises a shaft assembly rotation mechanism. In the illustrated expression, for example, the surgical tool 5000 comprises a rotation hub 12100 coupled to spool 8101a. A first end of a cable 12150 is fixedly attached to a superior portion rotation hub 12100a. Cable 12150 encircles and rotatingly engages shaft coupler or spool 12115 where shaft coupler is fixedly attached to shaft 5001. A second end of cable 12150 is fixedly attached to an inferior portion 12100b of hub 12100. As shown, cable 12150 twice encircles shaft coupler 12115 to permit 720° of rotation in one direction. The hub-cable-coupler assembly controls rotation of the shaft assembly 5001 in a clockwise (CW) and counter-clockwise (CCW) direction based on the rotational direction of the hub 12100. Accordingly, rotation of the hub 12100 about a first axis is converted to rotation of the coupler 12115 about a second axis, which is orthogonal to the first axis. As shown in FIGS. 13A and 13B, for example, a CCW rotation of the spool 8010a results in the hub 12100 rotating in a CCW direction which in turn places tension on cable 12150 at hub inferior portion 12100b. This tension on cable 12110 at hub inferior portion 12100b causes shaft coupler to rotate in a CW direction as indicated in FIG. 13A. Likewise, CW rotation of hub 12100 places tension on cable 12150 at superior hub end 12100a causing CCW rotation of spool 12115 thereby causing CCW rotation of coupler 8050 and concomitant CCW rotation of shaft 5001. It is appreciated that the spool 8010a may be rotated incrementally to provide precise rotation of the shaft. Such precise rotation may be enabled by an electrical interface between the user console 1000 and clip applier 5000 driven by a software algorithm, as is known and understood in the art. Shaft 5001 may be rotatably fixed to mounting assembly 5010 by means of clamp 8040, comprised of clamp halves 8040*a* and 8040*b*. Shaft 5001 is provided with a shaft collar 8050 that is fixedly attached to shaft 5001 and coupler 12115 that permits transfer of rotational force to shaft 5001. Clamp halves 8040*a* and 8040*b* enclose shaft collar 8050 and are provided with recesses to permit free rotation of shaft 5001 while prohibiting shaft 5001 linear motion. In the present expression, clamp collar 8050 is a provided with an annular flange 8050*b* to mate with clamp 8040 recesses to prevent axial motion.

Figure 14A:
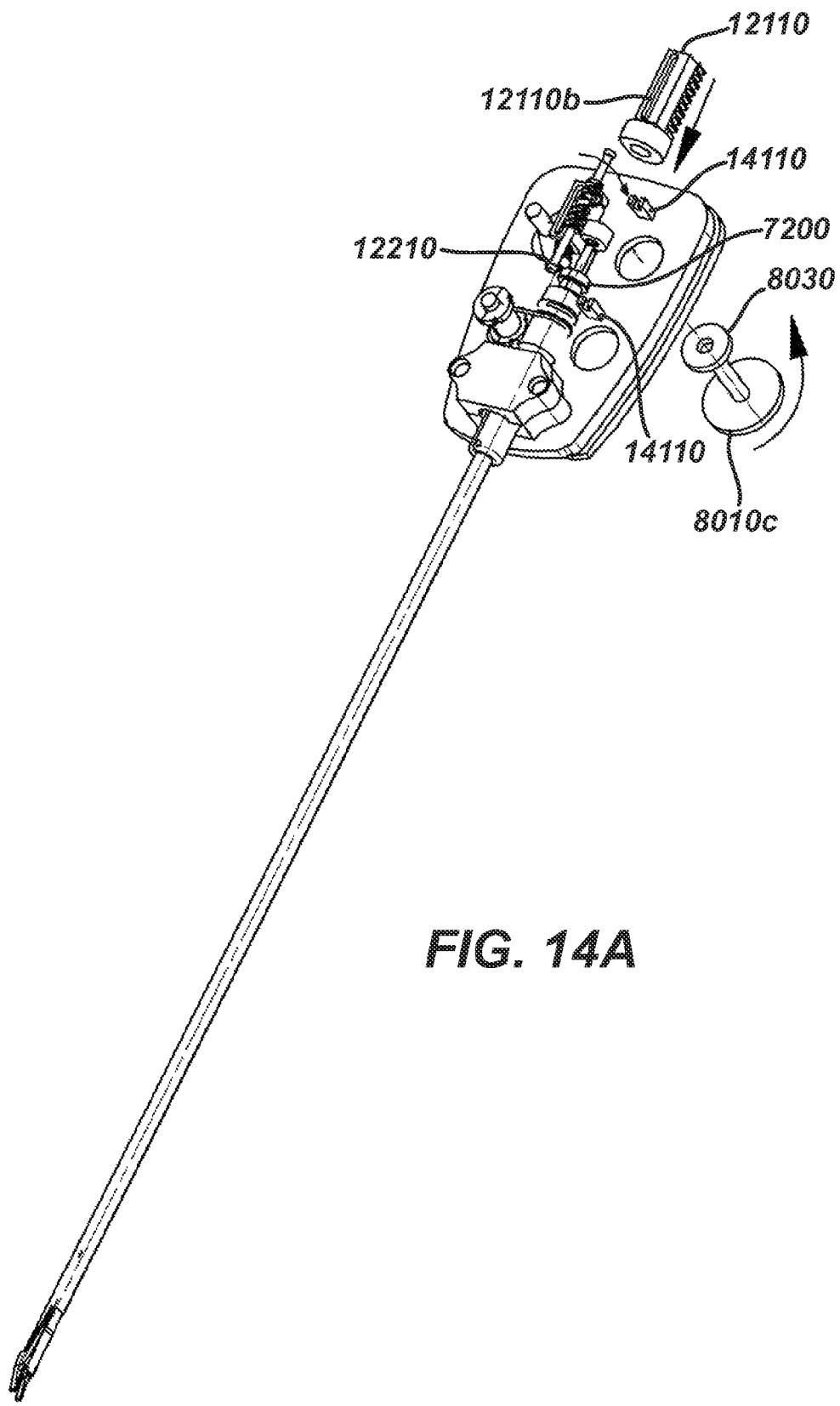
FIG. 14A is an assembly view of the FIG. 12 expression clip feed mechanism.
Figure 14B:
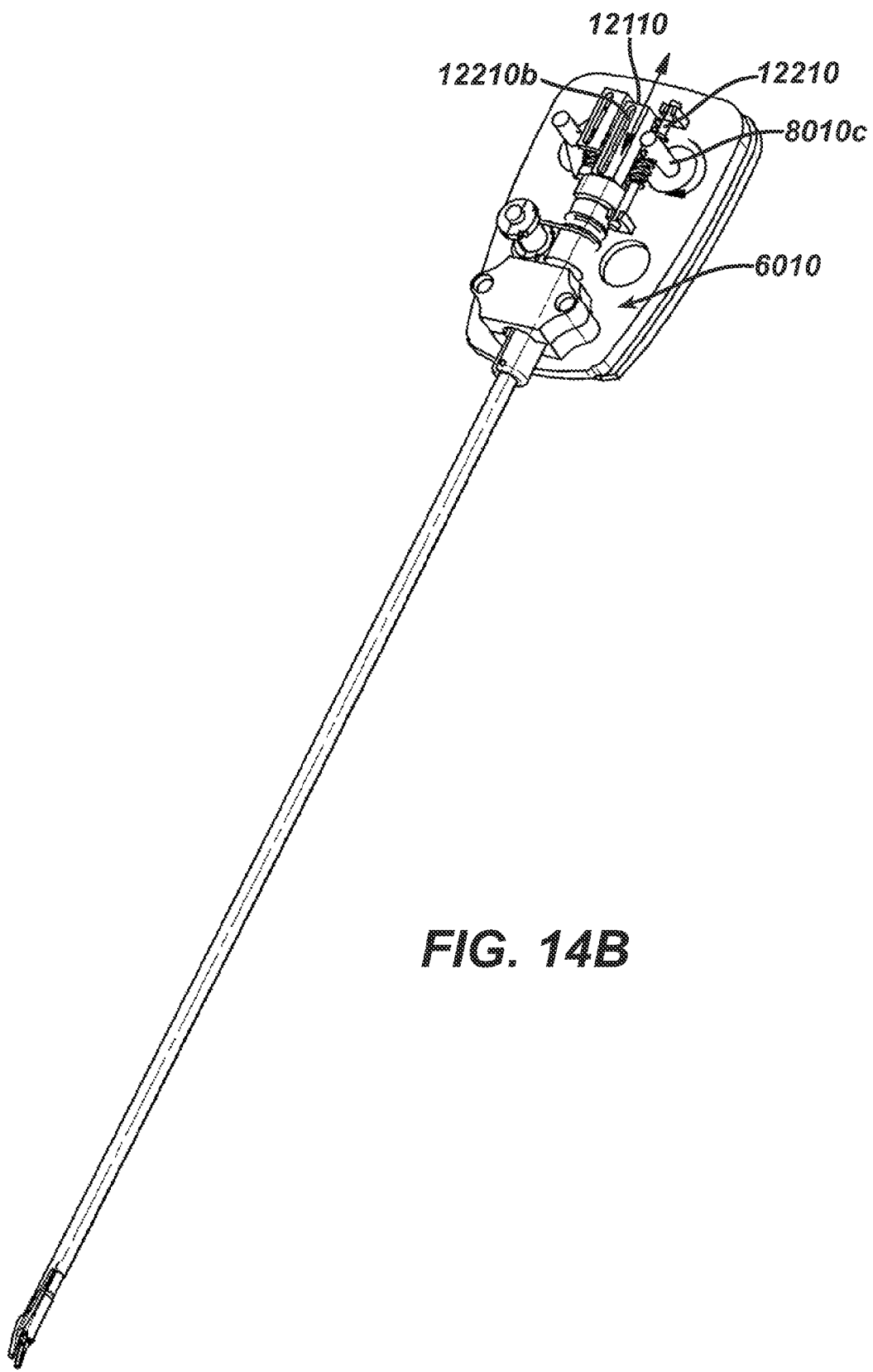
FIG. 14B is an isometric view of the FIG. 12 clip feeding mechanism in operation.

Still referring to the FIG. 12 expression, tool mounting portion 5003 of clip applier 5000 comprises a clip feed mechanism to feed clips into jaws 7060 as shown in FIGS. 14A and 14B. In the illustrated expression for example, the surgical tool 5000 comprises a rack 12110 and worm gear 12210 gearing mechanism to provide the clip feed functionality. Worm gear 12210 is comprised of helical threads mounted on a shaft where the shaft is rotatingly affixed to shaft mounts 14110. Mounts 14110 permit free rotation and prevent axial movement of worm gear 12210 shaft. Worm gear 12210 is coupled to a spool 8010*c* by a cable affixed to spool 8010*c* at superior and inferior locations (not shown) such that rotation of the corresponding driven element 6020 causes the spool 8010*c* to rotate applying tension selectively to worm gear 12210 cable at either the spool 8010*c* superior or inferior position depending upon spool rotation direction. As shown in the present expression, rack 12110 moves in a linear direction and is affixed to feed bar coupler 7200. In the FIG. 12 expression, the worm gear 12210 is meshed to a feed rack gear 12110, which moves in a linear direction. As shown, feeding rack 12110 is provided with a cut-out portion configured to nestle with a similar cut-out portion on forming rack Feed rack 12110 is configured with a rectangular outer surface wherein one side of the rectangular outer portion comprises the rack teeth. The feed rack 12110 further comprises a flange portion having a slot. Tool mounting portion is further provided with a rectangular pin located in cover 8000 adapted to mate with feed rack slot 12110*b* such that the mating of the pin and slot 12110*b* maintain rack 12110 in a fixed lateral position relative to tool mounting portion 5003 while permitting linear movement.

In operation, worm gear 12210 is meshed to feed rack 12110 such that when worm gear 12210 is rotated in a first or second direction, rack 12110 is moved linearly in a corresponding first or second direction. As shown in FIG. 14A, CCW rotation of spool 8010*c* selectively places tension on worm gear cable causing worm gear 12210 to rotate in a CW direction. CW rotation of worm gear 12210 imparts distal linear motion to rack 12110 which in turn moves feed bar coupler distally causing feed bar 7030 to move distally, as was described above. In the present expression, worm gear 12210 is rotated sufficiently to advance rack 12110 distally a sufficient distance to fully advance a clip into jaws 7060. Rack 12110 travel distance may vary based upon several factors e.g. clip leg length, jaw length. In the present expression, feed rack travels approximately 0.25 inches. Feed worm gear 12210 rotation may be precisely controlled by an electrical and software interface to deliver the exact feed rack 12110 travel necessary to feed a clip into the jaws 7060. Upon delivery of a clip into the jaws or after a predetermined amount of rotation of feed worm gear 12210, rotation of worm gear 12210 is reversed to a CW direction to move feed rack 12110 in a proximal direction, in turn moving feedbar coupler 7200 proximally, which in turn moves feedbar 7030 proximally, as was described above. This process may be repeated several times to accommodate a predetermined number of clips residing in the shaft. The software interface may be programmed to count down the number of clips fed into the jaws and display the same to the user and may further prevent the user from attempting to feed another clip once the shaft is empty. It is contemplated that the software interface may alert the user when the shaft contains a predetermined amount of clips.

Referring back to FIG. 12 and FIGS. 15A and 15B, tool mounting portion 5003 of clip applier 5010 comprises a clip forming mechanism to form clips in jaws 7060. In the illustrated expression for example, the surgical tool 5000 comprises a rack and worm gearing mechanism to provide the clip forming functionality. A forming worm gear 12300 is comprised of helical teeth mounted to a shaft 12330 (see FIG. 15A) where shaft 12330 is mounted to a bell crank 12320. Worm gear 12300 is coupled to a spool 8010*b* at superior and inferior portions of spool 8010*b* shaft by a cable 12310 such that rotation of the corresponding driven element 6020 causes the spool 8010*b* and worm gear 12300 to rotate in a first direction. In the FIG. 12 expression, the worm gear 12300 is meshed to a feed rack gear 12200, which moves in a linear direction. This mesh arrangement prevents bell crank 12320 and worm gear 12300 from rotating when spool 8010*b* is rotated. The rack gear 12200 is coupled to male end 7130*b* of pushrod 7130. Forming rack 12200 is configured with a rectangular outer surface where a side of the outer surface comprises rack teeth which are adapted to mesh with helical teeth of worm gear 12300. The forming rack 12200 further comprises a flange portion having a slot 12200*b*. Tool mounting portion is further provided with a rectangular pin located in cover 8000 adapted to mate with feed rack slot 12200*b* such that the mating of the pin and slot 12200*b* maintain rack 12200 in a fixed lateral position relative to shaft 5001 central axis.

Figure 15A:
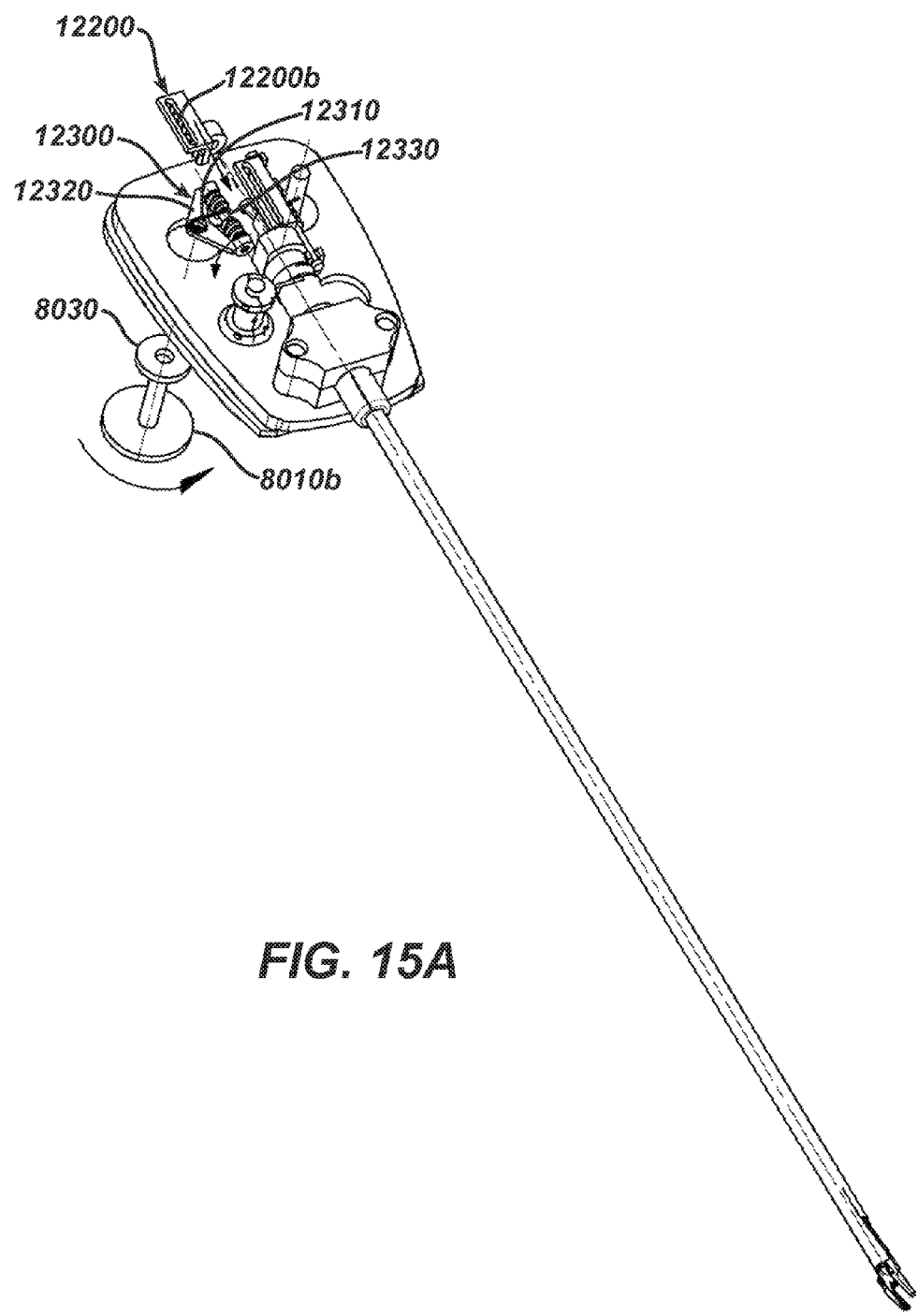
FIG. 15A is an assembly view of the FIG. 12 expression clip forming mechanism.
Figure 15B:
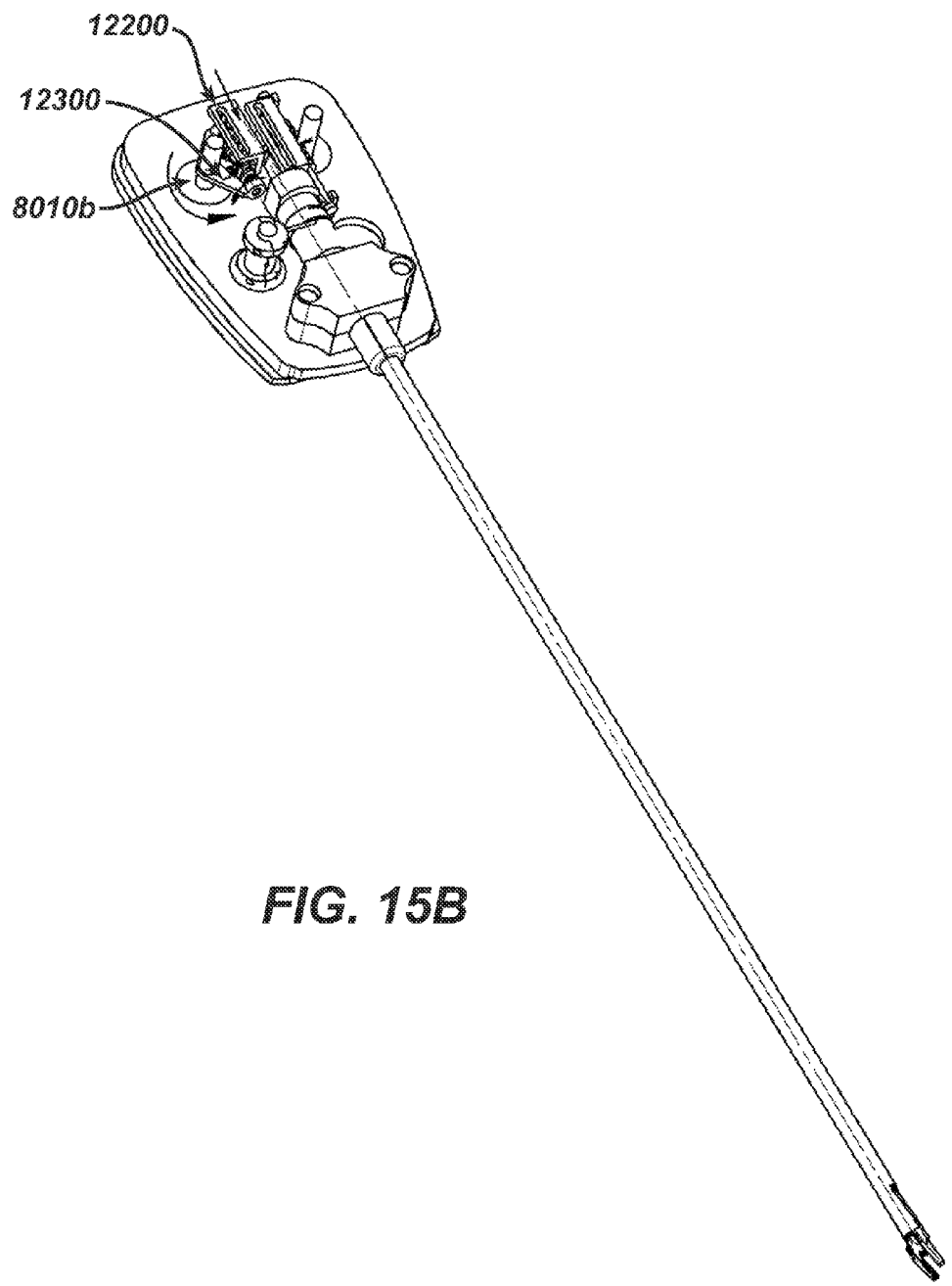
FIG. 15B is an isometric view of the FIG. 12 clip forming mechanism in operation.

In operation, referring now to FIGS. 15A and 15B, the form worm gear 12300 is encircled by a cable that is fixedly attached to inferior and superior portions of spool 8010*b* and is meshed with rack 12200 in tool mounting portion 5003. Once the feed function is complete and a clip is present in jaws, spool 8010*b* rotates in a CCW direction imparting CCW rotation to worm gear 12300 which in turn drives rack 12200 in a distal linear direction. Such distal linear motion of rack 12200 drives pushrod 7130 in a distal linear direction which drives cam 7120 over jaws 7060 crimping a clip, as was described above.

Rotation of worm gear 12300 may be precisely controlled to impart a sufficient number of rotations to advance rack 12200 a predetermined distance to fully form a clip. Alternatively, worm gear 12300 may be rotated slowly and stopped to permit partial formation of a clip about an anatomic structure which enables movement of the clip in a less than fully formed state about an anatomic structure. Once a clip deployment location is selected, worm gear 12300 may be rotated such that a clip is fully formed, occluding an anatomic structure. Once a clip is deployed, spool 8010*b* is driven in a CW direction which in turn rotates worm gear 12300 in a CW direction, which drives rack 12200 in a proximal direction, moving pushrod 7130 proximally which drives cam 7120 proximally, permitting jaws 7060 to open. It is contemplated that jaw 7060 opening and closing may be performed independently of clip feeding, thus allowing a user to utilize clip applier 5000 as a dissector.

Figure 16:
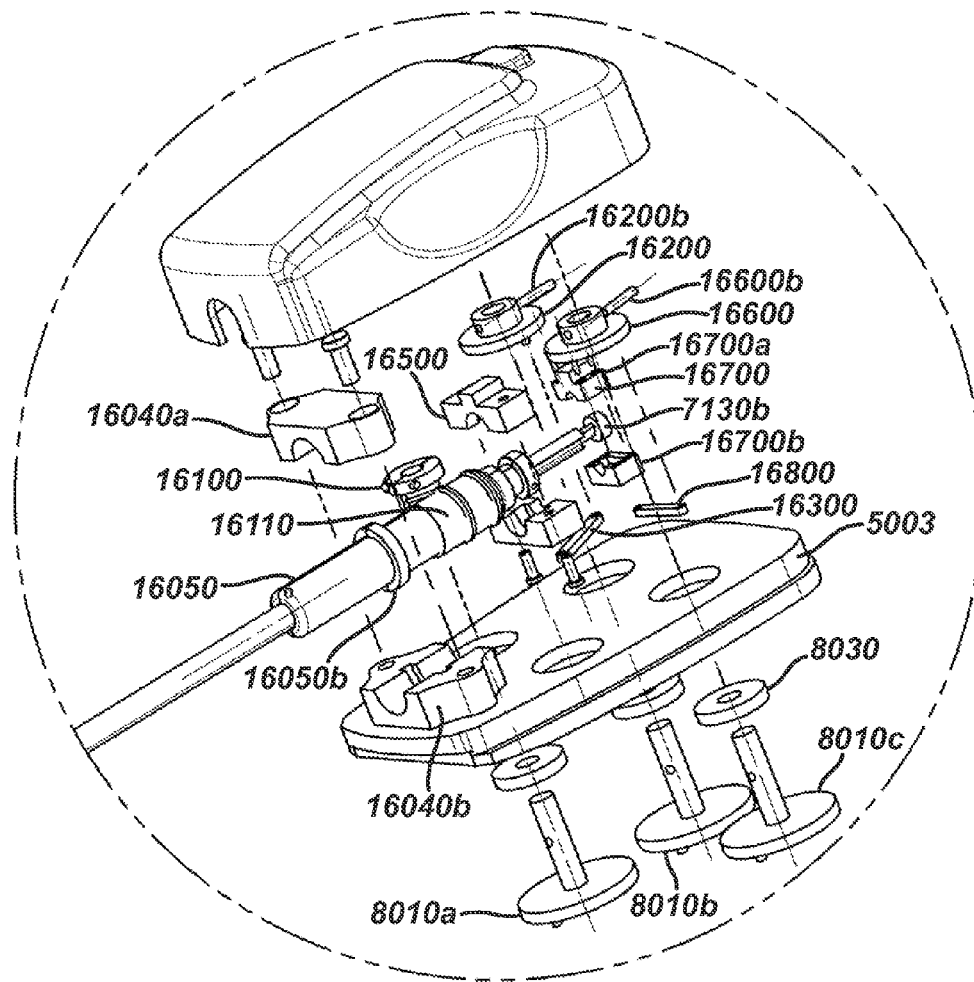
FIG. 16 is an exploded view of a third expression of a surgical tool drive assembly adapted for use with a robotic surgical system.

Referring now to FIG. 16, an exploded view of a third expression of the present clip applier 5000 is shown. In this expression, the clip applier 5000 includes rotatable bodies or spools 8010*a*, 8010*b*, 8010*c* and are coupled to rotatable bodies or drive elements 6020. The spools 8010*a,b,c* may be formed integrally with the driven elements 6020. In other expressions, spools may be formed separately from the driven elements 6020 provided that the spools 8010*a,b,c* and the elements 6020 are fixedly coupled such that driving the elements 6020 causes rotation of the spools 8010*a,b,c*. Each spool 8010*a,b,c* is coupled to a gear train or drive assembly for translating motion to the shaft 7010 for rotating the shaft, advancing a clip and forming a clip. As shown, spools 8010*a,b,c* interface with spool bearings 8030 seated between spools 8010*a,b,c* and mounting plate 5003 to facilitate smooth transfer of rotational forced from corresponding drive elements on the robotic arm 2006. The bearings 8030 may further be provided to support and stabilize the mounting of spools 8010*a,b,c* and reduce rotary friction of shaft and gears, for example.

Figure 17A:
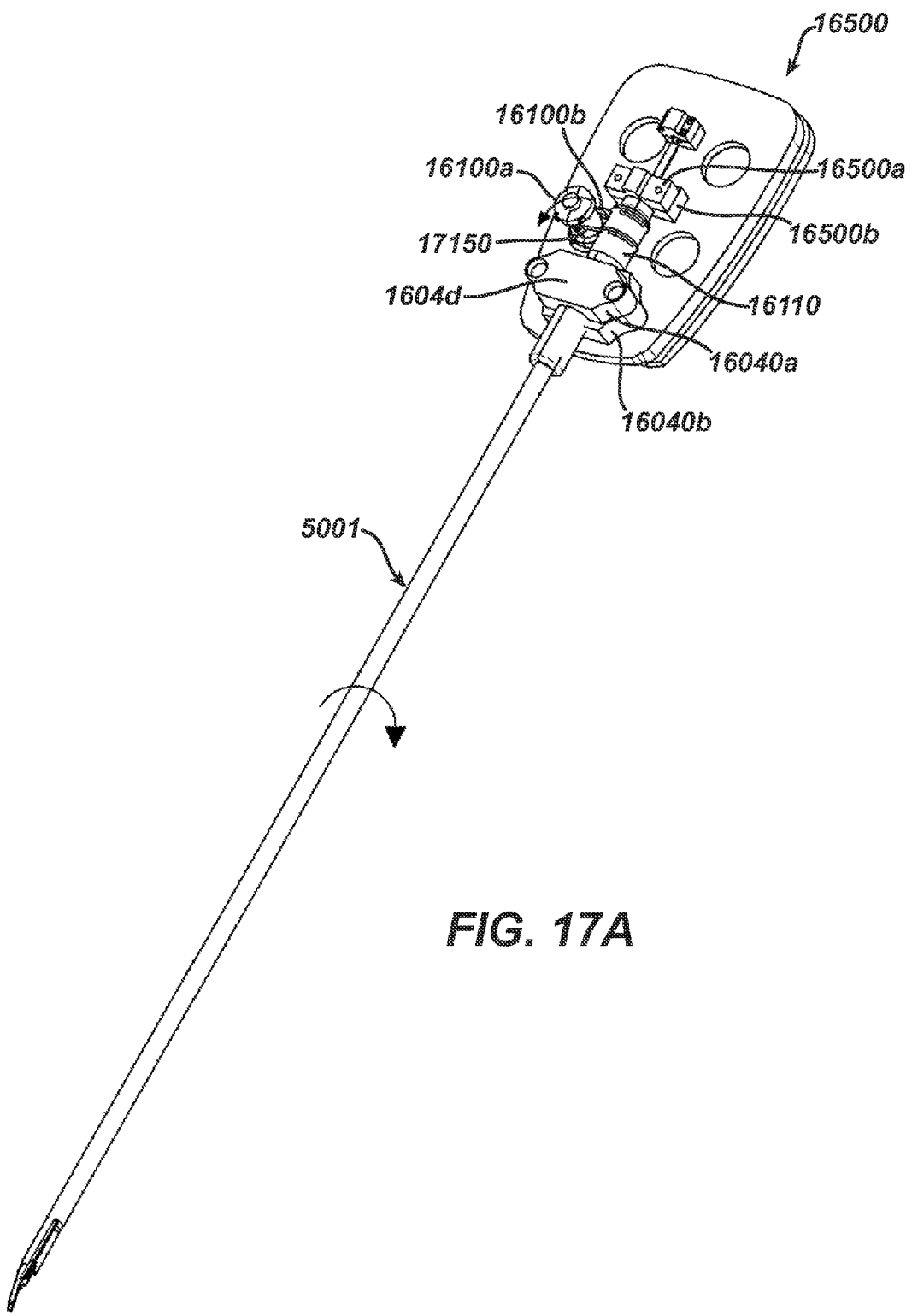
FIG. 17A is an assembly view of the FIG. 16 expression rotation mechanism.
Figure 17B:
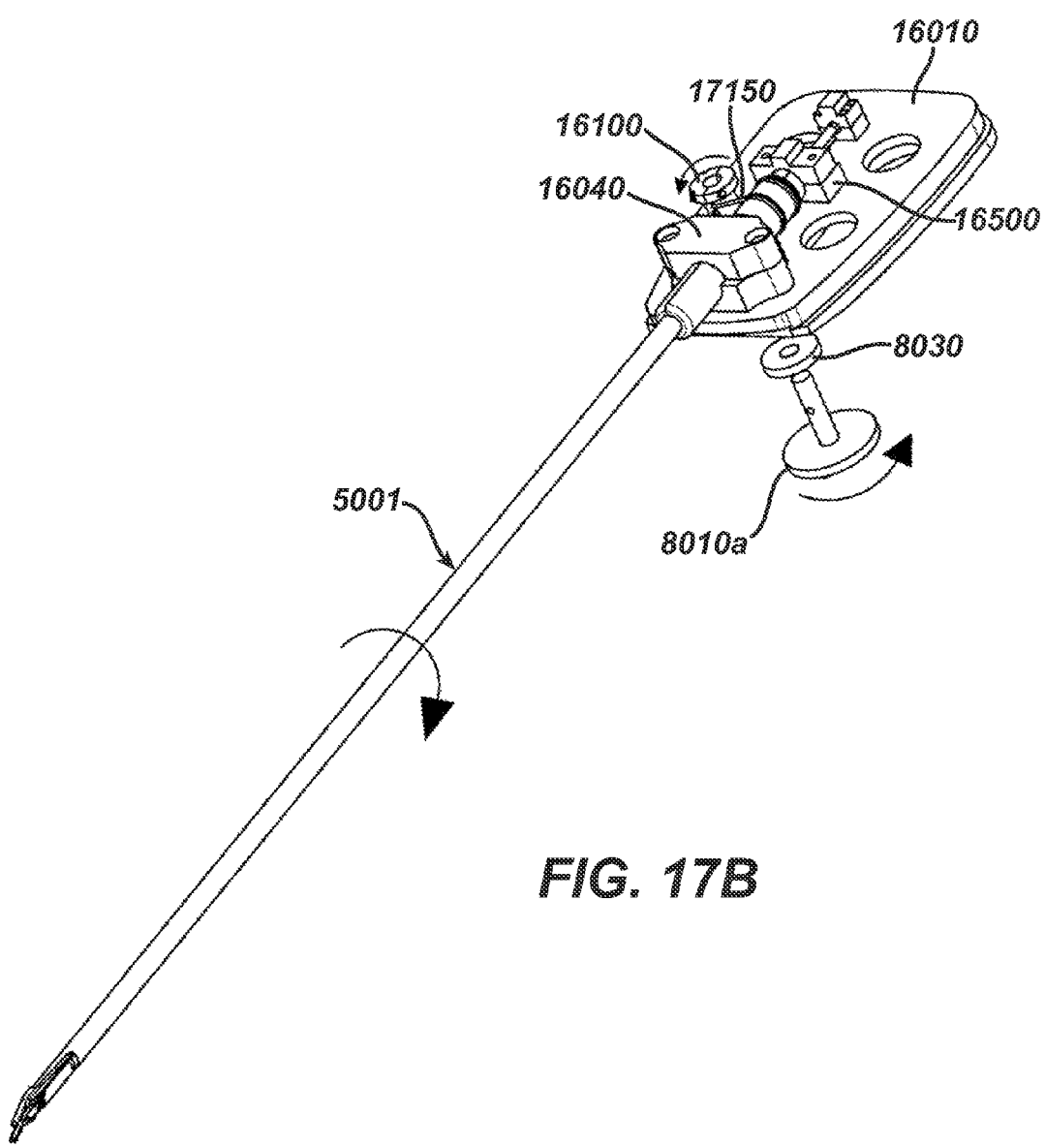
FIG. 17B is an isometric view of the FIG. 16 rotation mechanism in operation.

In the FIG. 16 expression, the tool mounting portion 5003 of the clip applier 5000 comprises a shaft assembly rotation mechanism. In the illustrated expression, for example, the surgical tool 5000 comprises a rotation hub 16100 coupled to spool or pulley 16110 by cable 17150 (see FIG. 17A). A first end of a cable 17150 is fixedly attached to a superior portion rotation hub 16100*a*. Cable 17150 encircles and rotatingly engages shaft coupler or spool 16110 where shaft coupler is fixedly attached to shaft 5001. A second end of cable 17150 is fixedly attached to an inferior portion 16100*b* of hub 16100. As shown, cable 17150 twice encircles shaft coupler 16110 to permit 720° of rotation in one direction. The hub-cable-coupler assembly controls rotation of the shaft assembly 5001 in a clockwise (CW) and counter-clockwise (CCW) direction based on the rotational direction of the hub 16100. Accordingly, rotation of the hub 16100 about a first axis is converted to rotation of the coupler 16110 about a second axis, which is orthogonal to the first axis. As shown in FIGS. 17A and 17B, for example, a CCW rotation of the spool 8010*a* results in the hub 16100 rotating in a CCW direction which in turn places tension on cable 17150 at hub inferior portion 16100*b*. This tension on cable 17150 at hub inferior portion 16100*b* causes shaft coupler to rotate in a CW direction as indicated in FIG. 17A. Likewise, CW rotation of hub 16100 places tension on cable 12110 at superior hub end 16100*a* causing CCW rotation of spool 16100 thereby causing CCW rotation of coupler or spool 16110 and concomitant CCW rotation of shaft 5001. It is appreciated that the spool 8010*a* may be rotated incrementally to provide precise rotation of the shaft. Such precise rotation may be enabled by an electrical interface between the user console 1000 and clip applier 5000 driven by a software algorithm, as is known and understood in the art. Shaft 5001 may be rotatably fixed to mounting assembly 5010 by means of clamp 16040, comprised of clamp halves 16040*a* and 16040*b*. Shaft 5001 is provided with a shaft collar 16050 that is fixedly attached to shaft 5001 and coupler or spool 16110 that permits transfer of rotational force to shaft 5001. Clamp halves 16040*a* and 16040*b* enclose shaft collar 16050 and are provided with recesses to permit free rotation of shaft 5001 while prohibiting shaft 5001 linear motion. In the present expression, clamp collar 16050 is a provided with an annular fl-angel 16050*b* to mate with clamp 8040 recesses to prevent axial motion while permitting rotation.

Still referring to the FIG. 16 expression, tool mounting portion 5003 of clip applier 5010 comprises a clip feed mechanism to feed clips into jaws 7060. In the illustrated expression for example, the surgical tool 5000 comprises a feeding crank, connecting rod and slider assembly to provide the clip feed functionality. A feeding crank 16200 is coupled to a spool 8010*b* by pin 16200*b* such that rotation of the corresponding driven element 6020 causes the spool 8010*b* and feed crank 16200 to rotate in a first direction. In the FIG. 16 expression, the feed crank 16200 is a circular crank connected to feed slider 16500 via feed connecting rod 16300, where angular motion of feed crank 16200 is converted to feed slider 16500 linear motion via connecting rod 16300. The feeding slider 16500 is coupled to feed bar coupler 7200 by substantially encircling coupler 7200 where slider 16500 is provided with angular recesses that mate with coupler 7200 angular flanges. Coupler 7200 is fixedly attached to feedbar 7030, as was described above.

Figure 18A:
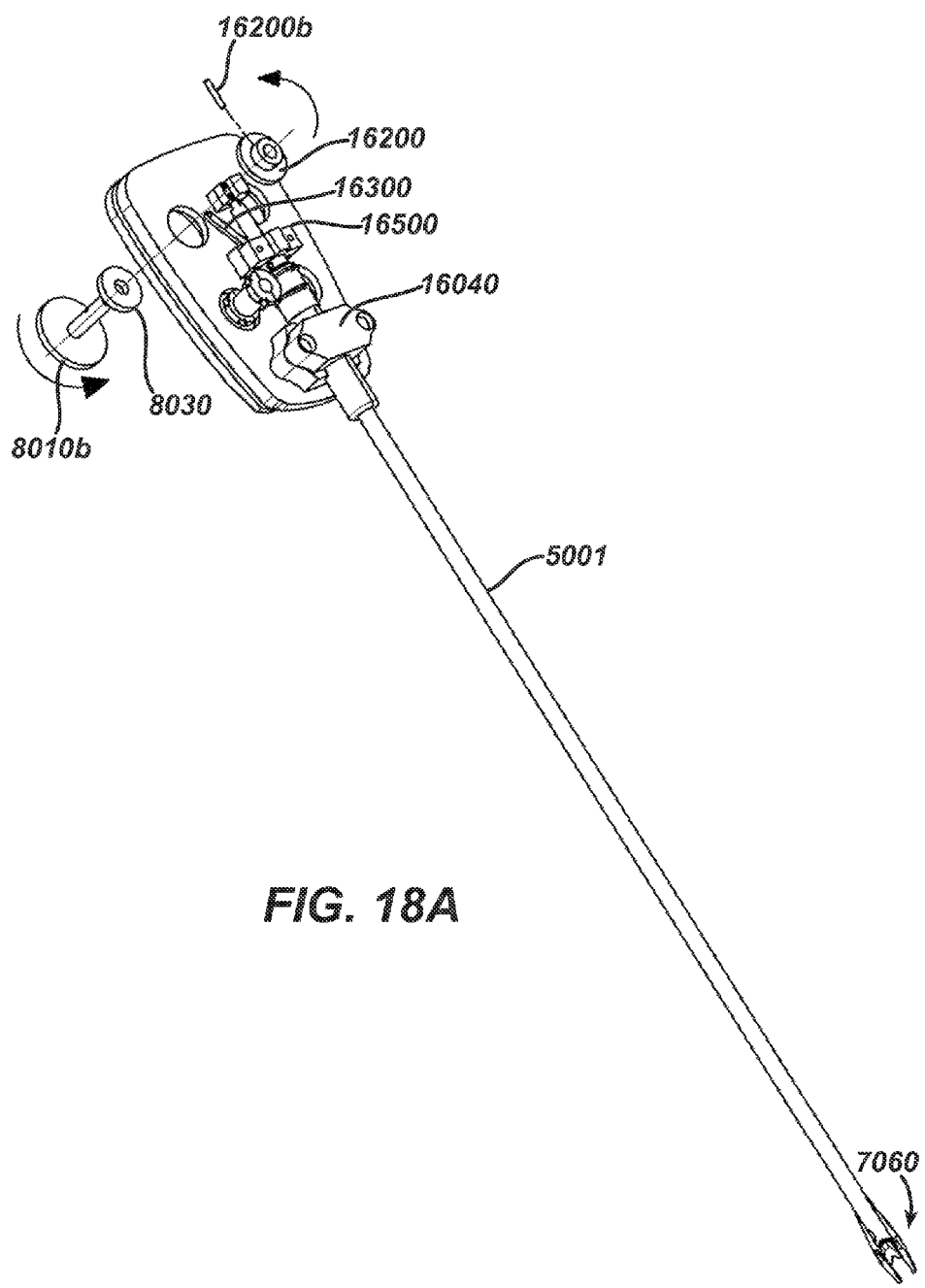
FIG. 18A is an assembly view of the FIG. 16 expression clip feed mechanism.
Figure 18B:
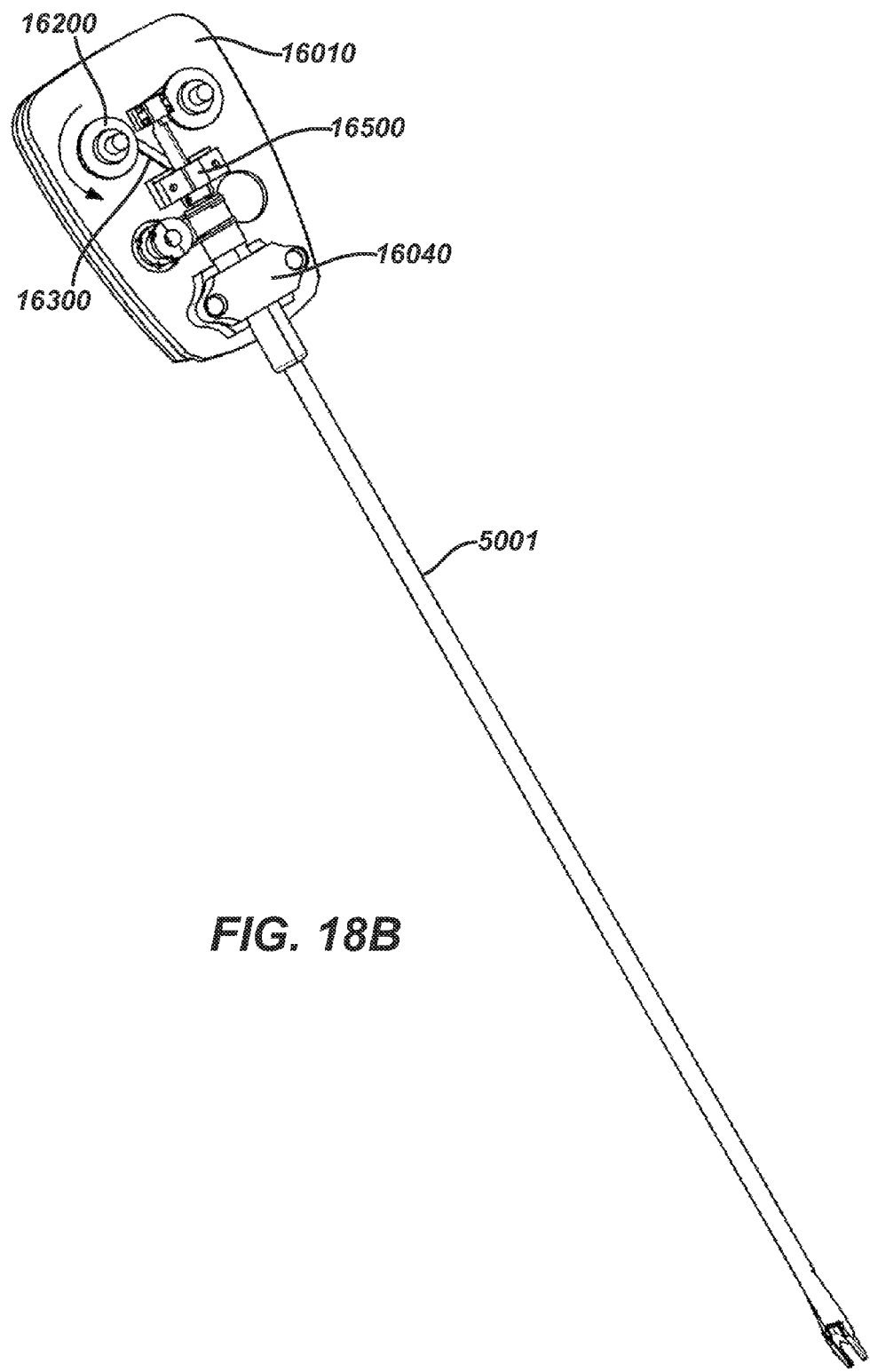
FIG. 18B is an isometric view of the FIG. 16 clip feeding mechanism in operation.

In operation, referring to FIGS. 18A and 18B, the feed crank 16200 is connected to feed slider 16500 via connecting rod 16300 in tool mounting portion 5003. Feed spool 8010*b* is rotated in a CCW direction which in turn rotates feed crank 16200 in a counter-clockwise direction. In the FIG. 18A expression, feed connecting rod 16300 is connected to feed crank 16200 on a side opposite an axis defined by shaft 5001. In this arrangement, CCW rotation of crank 16200 causes connecting rod 16300 to move in a distal direction thereby causing slider 16500 to move distally, causing feed bar 7030 to move distally, advancing a clip into jaws 7060. In the present expression, feed crank 16200 is rotated sufficiently to move connecting rod 16300 and slider 16500 distally a sufficient distance to fully advance a clip into the jaws 7060. Slider 16500 travel distance may vary based upon several factors e.g. clip leg length, jaw length. In the present expression, feed rack travels approximately 0.25 inches. Feed crank 16200 rotation may be precisely controlled by an electrical and software interface to deliver the exact feed slider 16500 travel necessary to feed a clip into the jaws 7060. Upon delivery of a clip into the jaws or after a predetermined amount of rotation of feed crank 16200, rotation of crank 16200 is reversed to a CW direction to move feed connecting rod 16300 and slider 16500 in a proximal direction, in turn moving feedbar coupler 7200 proximally, which in turn moves feedbar 7030 proximally, as was described above. This process may be repeated several times to accommodate a predetermined number of clips residing in the shaft. The software interface may be programmed to count down the number of clips fed into the jaws and display the same to the user and may further prevent the user from attempting to feed another clip once the shaft is empty. It is contemplated that the software interface may alert the user when the shaft contains a predetermined amount of clips.

Referring back to FIG. 16, tool mounting portion 5003 of clip applier 5000 comprises a clip forming mechanism to form clips in jaws 7060. In the illustrated expression for example, the surgical tool 5000 comprises a crank, connecting rod and forming slider to provide the clip forming functionality. Forming crank 16600 is coupled to spool 8010*c* by pin 16600*b* such that rotation of the corresponding driven element 6020 causes the spool 8010*b* and forming crank 16600 to rotate in a first direction. In the FIG. 16 expression, the forming crank 1600 is in mechanical communication with form slider 16700 via form crank. Angular rotation of crank 16600 causes linear motion of connecting rod 16800 which moves form slider 16700 in a linear direction. Form slider 16700 is comprised of slider halves 16700*a* and 16700*b* that substantially enclose about and couple to male end 7130*b* of pushrod 7130 as was described above.

Figure 19A:
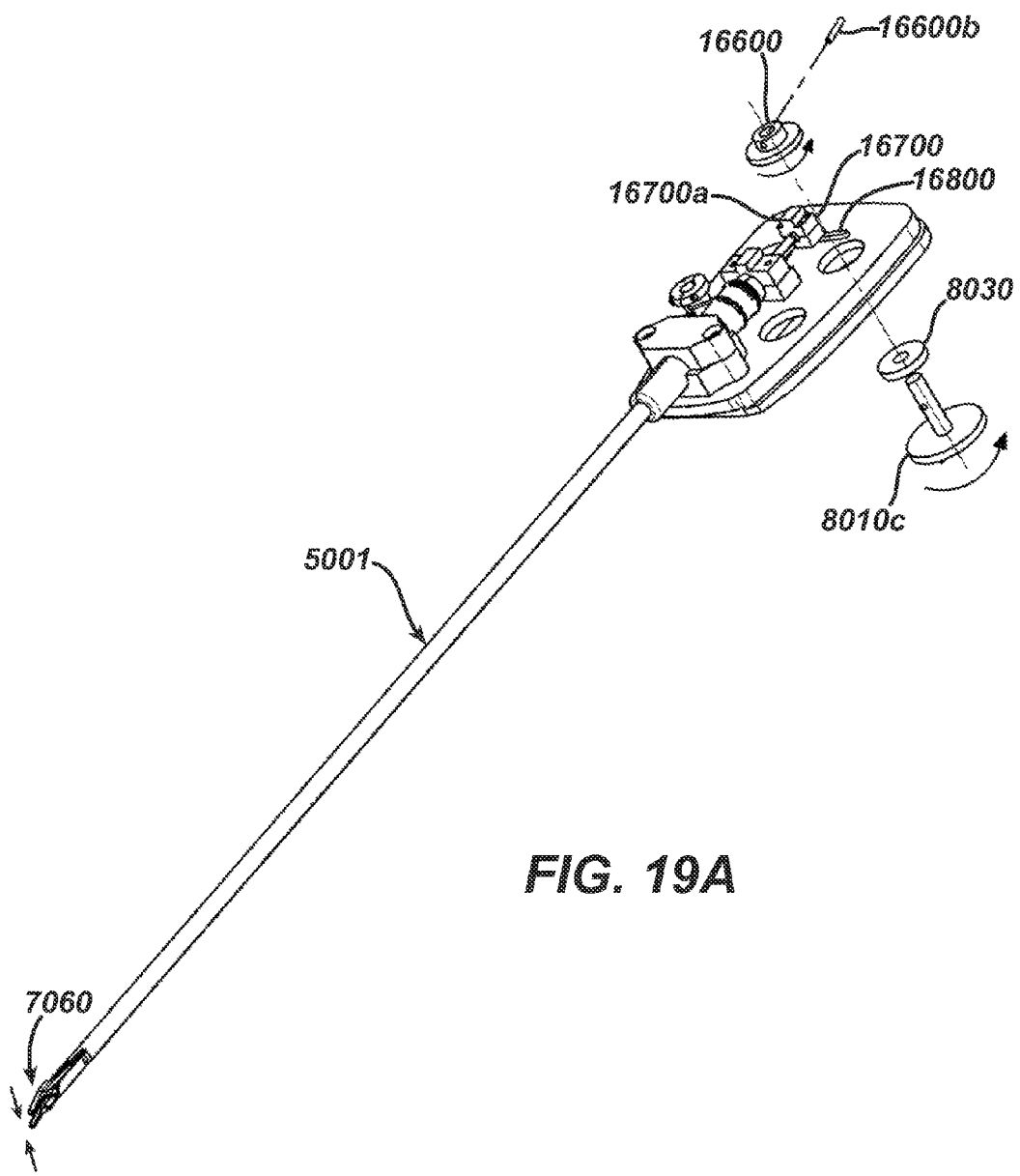
FIG. 19A is an assembly view of the FIG. 16 expression clip forming mechanism.
Figure 19B:
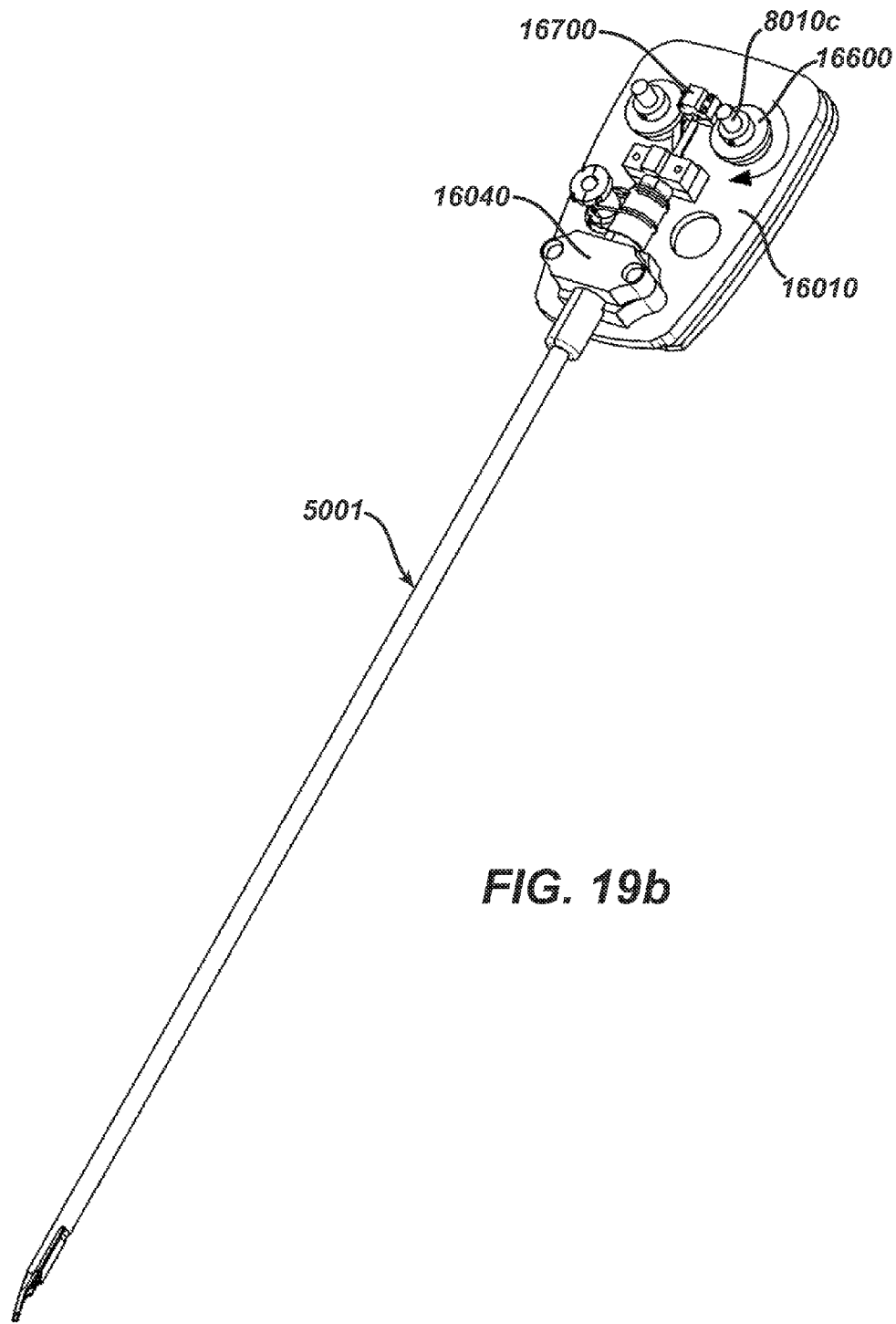
FIG. 19B is an isometric view of the FIG. 16 clip forming mechanism in operation.

In operation, referring now to FIGS. 19A and 19B, the form crank 16600 is fixedly attached to spool 8010*b* by pin 16600*b* in tool mounting portion 5003. Once the feed function is complete and a clip is present in jaws, spool 8010*c* rotates in a CCW direction imparting CCW rotation to form crank 16600. Connecting rod 16800 is affixed to crank 16600 on a surface between spool 8010*c* shaft and clip applier shaft 5001 such that CCW rotation of crank 16600 imparts distal linear motion (in a direction towards jaws 7060) to forming connecting rod 16800. Distal linear movement of connecting rod 16800 pulls form slider 16700 in a distal linear direction which drives pushrod 7130 in a distal linear direction which drives cam 7120 over jaws 7060 thereby crimping a clip in the jaws 7060, as was described above.

Rotation of crank 16600 may be precisely controlled to impart a sufficient number of rotations to move connecting rod 16800 and slider 16700 a predetermined distance to fully form a clip. Alternatively, crank 16600 may be rotated slowly and stopped to permit partial formation of a clip about an anatomic structure which enables movement of the clip in a less than fully formed state about an anatomic structure. Once a clip deployment location is selected, crank 16600 may be rotated such that a clip is fully formed, occluding an anatomic structure. Once a clip is deployed, crank 16600 is rotated in a CW direction, connecting rod 16800 and slider 16700 in a proximal direction, moving pushrod 7130 proximally which drives cam 7120 proximally, permitting jaws 7060 to open. It is contemplated that jaw 7060 opening and closing may be performed independently of clip feeding, thus allowing a user to utilize clip applier 5000 as a dissector.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While the examples herein are described mainly in the context of mechanical clip applier instruments, it should be understood that the teachings herein may be readily applied to a variety of other types of medical instruments. By way of example only, the teachings herein may be readily applied to tissue graspers, tissue scissors, surgical dissectors, or a variety of energy based surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments or expressions of devices and components thereof disclosed herein have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of devices and components thereof, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

While certain features of the aspects have been illustrated as described herein, many modifications, substitutions, changes and equivalents will now occur to those skilled in the art. It is therefore to be understood that the appended claims are intended to cover all such modifications and changes as fall within the true scope of the disclosed embodiments.

We claim:

1. A surgical fastening instrument comprising:
   an end effector having a jaw assembly capable of supporting and deploying a fastener onto tissue;
   a shaft assembly capable of rotation about an axis operably interfacing with the end effector for transmitting an actuation motion to the end effector where the shaft assembly contains at least one fastener;
   a jaw closure cam disposed substantially about the jaw assembly, the jaw closure cam moving relative to the jaw assembly;
   a gear drive train connected to the shaft assembly, the gear drive train configured to receive power and control from a robotic system, the gear drive train adapted to separately control rotation of the shaft assembly, opening and closing of the jaws and advancement of the fastener from the shaft into the jaw assembly, the gear drive train comprising (i) a first pinion coupled to a first robotic input, the first pinion in mechanical communication with a worm gear where the worm gear is affixed to the shaft assembly such that rotation of the pinion in a first direction rotates the shaft assembly in a first direction;

(ii) a second pinion coupled to a second robotic input, the second pinion in mechanical communication with a first rack where the first rack is in mechanical communication with a fastener feed assembly such that rotation of the second pinion in a first direction moves the first rack in a first linear direction advancing the fastener in the shaft assembly; and (iii) a third pinion coupled to a third robotic input, the third pinion in mechanical communication with a second rack where the second rack is in mechanical communication with a jaw open and close assembly such that rotation of the third pinion in a second direction moves the second rack in a second linear direction actuating the jaw open and close assembly;

wherein the first, second, and third pinions are each adapted to rotate independent of the other pinions.

\* \* \* \* \*